(12) United States Patent
Oren et al.

(10) Patent No.: US 11,410,756 B2
(45) Date of Patent: Aug. 9, 2022

(54) SYSTEM AND METHOD FOR PREDICTING AND SUMMARIZING MEDICAL EVENTS FROM ELECTRONIC HEALTH RECORDS

(71) Applicant: Google LLC, Mountain View, CA (US)

(72) Inventors: Eyal Oren, Los Gatos, CA (US); Yingwei Cui, Palo Alto, CA (US); Gerardo Flores, Mountain View, CA (US); Gavin Duggan, Mountain View, CA (US); Kun Zhang, Mountain View, CA (US); Kurt Litsch, Mountain View, CA (US); Patrik Sundberg, San Francisco, CA (US); Yi Zhang, Sunnyvale, CA (US)

(73) Assignee: Google LLC, Mountain View, CA (US)

( * ) Notice: Subject to any disclaimer, the term of this patent is extended or adjusted under 35 U.S.C. 154(b) by 734 days.

(21) Appl. No.: 15/690,714

(22) Filed: Aug. 30, 2017

(65) Prior Publication Data

US 2019/0034590 A1     Jan. 31, 2019

Related U.S. Application Data

(60) Provisional application No. 62/538,112, filed on Jul. 28, 2017.

(51) Int. Cl.
*G16H 50/30* (2018.01)
*G16H 50/20* (2018.01)
(Continued)

(52) U.S. Cl.
CPC .......... *G16H 10/60* (2018.01); *G06N 3/0445* (2013.01); *G06N 3/0454* (2013.01); *G06N 3/08* (2013.01);
(Continued)

(58) Field of Classification Search
CPC ........ G16H 10/60; G16H 15/00; G16H 50/20; G16H 50/30; G06N 3/08; G06N 3/0445; G06N 3/0454
See application file for complete search history.

(56) References Cited

U.S. PATENT DOCUMENTS

| 10,468,126 B1 | 11/2019 | Harding et al. |
| 2003/0120514 A1* | 6/2003 | Rao ........................ G16H 70/60 705/2 |

(Continued)

FOREIGN PATENT DOCUMENTS

| CN | 104766127 A | 7/2015 |
| CN | 106815785 A | 6/2017 |

(Continued)

OTHER PUBLICATIONS

Miotto et al., Deep Patient: an unsupervised representation to predict the future of patients from electronic health records. Scientific Reports, May 2016 (Year: 2016).*

(Continued)

*Primary Examiner* — Jonathan Durant
(74) *Attorney, Agent, or Firm* — McDonnell Boehnen Hulbert & Berghoff LLP

(57) ABSTRACT

A system for predicting and summarizing medical events from electronic health records includes a computer memory storing aggregated electronic health records from a multitude of patients of diverse age, health conditions, and demographics including medications, laboratory values, diagnoses, vital signs, and medical notes. The aggregated electronic health records are converted into a single standardized data structure format and ordered arrangement per patient, e.g., into a chronological order. A computer (or computer system) executes one or more deep learning models trained on the aggregated health records to predict one or more future clinical events and summarize pertinent (Continued)

past medical events related to the predicted events on an input electronic health record of a patient having the standardized data structure format and ordered into a chronological order. An electronic device configured with a healthcare provider-facing interface displays the predicted one or more future clinical events and the pertinent past medical events of the patient.

8 Claims, 24 Drawing Sheets

(51) Int. Cl.
   *G16H 10/60* (2018.01)
   *G06N 3/08* (2006.01)
   *G16H 15/00* (2018.01)
   *G06N 3/04* (2006.01)

(52) U.S. Cl.
   CPC ............. *G16H 15/00* (2018.01); *G16H 50/30* (2018.01); *G16H 50/20* (2018.01)

(56) References Cited

U.S. PATENT DOCUMENTS

| | | | |
|---|---|---|---|
| 2007/0016450 | A1† | 1/2007 | Bhora |
| 2012/0209082 | A1 | 8/2012 | Al-Ali |
| 2014/0095201 | A1† | 4/2014 | Farooq et al. |
| 2015/0006088 | A1 | 1/2015 | Eshelman et al. |
| 2015/0025329 | A1 | 1/2015 | Amarasingham et al. |
| 2015/0254555 | A1 | 9/2015 | Williams, Jr. et al. |
| 2017/0004279 | A1* | 1/2017 | Pingali .................. G06Q 40/12 |
| 2017/0006135 | A1 | 1/2017 | Siebel et al. |
| 2017/0024642 | A1* | 1/2017 | Xiong .................... G06N 3/084 |
| 2017/0132371 | A1* | 5/2017 | Amarasingham ....... G06F 40/30 |
| 2017/0161439 | A1† | 6/2017 | Raduchel et al. |
| 2017/0329905 | A1* | 11/2017 | Passerini ................ G06N 20/00 |
| 2018/0068083 | A1* | 3/2018 | Cohen .................... G16H 50/20 |
| 2018/0137941 | A1* | 5/2018 | Chen ........................ G06N 3/04 |
| 2018/0158552 | A1* | 6/2018 | Liu ...................... G06N 3/0454 |
| 2018/0211010 | A1* | 7/2018 | Malhotra ................. G06N 3/08 |
| 2019/0341133 | A1 | 11/2019 | Harding et al. |

FOREIGN PATENT DOCUMENTS

| | | |
|---|---|---|
| JP | 2017-502439 A | 1/2017 |
| JP | 2020529057 A | 10/2020 |
| WO | 2006/013320 A1 | 2/2006 |
| WO | 2015/082555 A1 | 6/2015 |

OTHER PUBLICATIONS

Tran, Tung, and Ramakanth Kavuluru. "Predicting mental conditions based on "history of present illness" in psychiatric notes with deep neural networks." Journal of biomedical informatics 75 (2017): S138-S148. (Year: 2017).*

Huynh et al (2016). Adverse Drug Reaction Classification With Deep Neural Networks. In: Proceedings of COLING 2016: Technical Papers, COLING, pp. 877-887. (Year: 2016).*

Adler-Milstein, et al., "Electronic Health Record Adoption in US Hospitals: Progress Continues, but Challenges Persist," Health Aff., vol. 34, No. 12, pp. 2174-2180, 2015.

Bahdanau, et al., "Neural Machine Translation by Jointly Learning to Align and Translate," arXiv, pp. 1409.0473, 2014.

Bates, et al., "Big data in healthcare: using analytics to identify and manage high-risk and high-cost patients," Health Aff ., vol. 33, No. , pp. 1123-1131, 2014.

Choi et al., "GRAM: Graph-based attention model for Healthcare Representation Learning," arXiv, vol. 3, pp. 1611.07012, cs.LG, Apr. 2017.

Choi, et al., "RETAIN: an Interpretable Predictive Model for Healthcare using Reverse Time Attention Mechanism," arXiv:1608.05745v3[cs.GL], Feb. 2017.

Goldstein, et al., "Opportunities and challenges in developing risk prediction models with electronic health records data: a systematic review," J Am Med Inform Assoc., vol. 24, No. 1, pp. 198-208, 2017.

Henry, et al., "Adoption of Electronic Health Record Systems among U.S. Non-Federal Acute Care Hospitals: 2008-2015, Office of the National Coordinator for Health Information Technology," ONC data brief, No. 35, May 2016.

Hersh, et al., "Caveats for the use of operational electronic health record data in comparative effectiveness research," Med Care. vol. 51, No. 8 Suppl 3, pp. S30-S37, 2013.

Hochreiter, et al., "Long Short-Term Memory," Neural Comput, pp. 1735-1780, 1997.

Holzinger, "Beyond Data Mining: Integrative Machine Learning for Harth Informatics," Editorial Paper, pp. 1-22, 2016.

Holzinger, "Interactive machine learning for health informatics: when do we need human-in-the-loop," Brain Informatics, Vo 3, pp. 119-131, 2016.

Kantarjian, et al., "Artificial Intelligence, Big Data, and Cancer," JAMA Oncol., vol. 1, No. 5, pp. 573-574., 2015.

Mandel, et al., "SMART on FHIR: a standards-based, interoperable apps platform for electronic health records," J Am Med Inform Assoc,. vol. 23, No. 5, pp. 899-908, 2016.

Newton, et al., "Validation of electronic medical record-based phenotyping algorithms: results and lessons learned from the eMERGE network," J Am Med Inform Assoc, vol. 20, No. e1, pp. e147-e154, 2013.

Obermeyer, et al., "Predicting the Future—Big Data, Machine Learning, and Clinical Medicine," N Engl J Med., vol. 375, No. 13, pp. 1216-1219, 2016.

Opmeer, "Electronic Health Records as Sources of Research Data," JAMA. vol. 315, No. 2, pp. 201-202., 2016.

Parikh, et al., Integrating Predictive Analytics Into High-Value Care: The Dawn of Precision Delivery, JAMA, vol. 315, No. 7, pp. 651-652, 2016.

Vaswani, et al., "Attention is all you need," arXiv, vol. 1706, pp. 03762 [cs.CL], 2017.

Zimmerman, et al., "Acute Physiology and Chronic Health Evaluation (APACHE) IV: hospital mortality assessment for today's critically ill patients," Crit. Care Med., 2006.

PCT International Search Report and Written Opinion, PCT International Application No. PCT/US2017/049300, dated Nov. 20, 2017, 27 pages.

Cheng, Yu et al., "Risk Prediction With Electronic Health Records: A Deep Learning Approach", Proceedings of the 2016 SIAM International Conference on Data Mining. Society for Industrial and Applied Mathematics, 2016, 9 pages.

Gegg-Harrison, Tim et al., "Porting a Cancer Treatment Prediction to a Mobile Device", Conf. Proc IEEE Eng. Med. Biol. Soc., pp. 1-10.

Lin, Jie et al., "A Prognostic Model to Predict Mortality Among Non-Small Cell Lung Cancer Patients in the U.S. Military Health System", J. Thorac. Oncol., Dec. 2015, pp. 1-17.

Pham, Trang et al., "Predicting Healthcare Trajectories From Medical Records: A Deep Learning Approach", Journal for Biomedical Informatics, vol. 69, 2017, pp. 218-229.

Ma, Fenglong et al., "Dipole: Diagnosis Prediction in Healthcare via Attention-Based Bidirectional Recurrent Neural Networks", Proceedings of the 23rd ACM SIGKDD International Conference on Knowledge Discovery and Data Mmining, ACM, 2017, 10 pages.

Jagannatha, Abhyuday N. et al., "Structured Prediction Models for RNN Based Sequence Labeling in Clinical Text", Proceedings of the Conference on Empirical Methods in Natural Language Processing. Conference on Empirical Methods in Natural Language Processing. vol. 2016. NIH Public Access, 2016, 10 pages.

Evans, R. Scott et al., "Automated Identification and Predictive Tools to Help Identify High-Risk Heart Failure Patients: Pilot Evaluation", Journal of American Medical Informatics Association, 2016, pp. 872-878.

(56) References Cited

OTHER PUBLICATIONS

Zhong, Hongye et al., "Enhancing Health Risk Prediction With Deep Learning on Big Data and Revised Fusion Node Paradigm", Scientific Programming, May 2017, pp. 1-18.
Devarakonda, Murthy et al., "Problem-Orientated Patient Record Summary: An Early Report on a Watson Application", 2014 IEEE 16th International Conference on E-Health Networking, Applications and Services (Healthcom), 2014, pp. 281-286.
Neuvirth, Hani et al., "Toward Personalized Care Management of Patients at Risk—The Diabetes Case Study", Proceedings of the 17th ACM SIGKDD International Conference on Knowledge Discovery and Data Mining. ACM, 2011, pp. 395-403.
Raffel, Colin et al., "Feed-Forward Networks With Attention Can Solve Some Long-Term Memory Problems", Workshop Track—ICLR 2016, pp. 1-6.
Taieb, Souhaib Ben et al., "Boosting Multi-Step Autoregressive Forecasts", ICML. 2014, 10 pages.
U.S. Appl. No. 62/039,059, filed Aug. 14, 2014.
U.S. Appl. No. 14/693,147, filed Apr. 22, 2015.
U.S. Appl. No. 16/776,412, filed Jan. 29, 2020.
The extended European Search Report for EP Application No. 17 91 9282 dated Dec. 21, 2020, pp. 1-17.
Choi, Edward et al. "RETAIN: An Interpretable Predictive Model for Healthcare using Reverse Time Attention Mechanism" (2016). XP055759133. Retrieved from the Internet: URL:https://arxiv.org/pdf/1608.05745v1.pdf [retrieved on Dec. 11, 2020].
Nguyen, Phuoc et al. "Deep Learning to Attend to Risk in ICU" arxiv.org. Cornell University Library (2017) XP080777173.
Ma, Fenglong et al. "Dipole: Diagnosis Prediction in Healthcare via Attention-based Bidirectional Recurrent Neural Networks" ARXIV. org, (Jun. 19, 2017) XP080770722, URL, DOI:10. 1145/3097983. 3098088.
Edward Choi, et al. "Doctor AI: Predicting Clinical Events via Recurrent Neural Networks" arXiv, Sep. 28, 2016, pp. 1-18.
Edward Choi, et al., RETAIN: An Interpretable Predictive Model for Healthcare using Reverse Time Attention Mechanism, arXiv, Feb. 26, 2017, pp. 1-13.
Tung Tran, "Predicting mental conditions based on history of present illness in psychiatric notes with deep neural networks". Journal of Biomedical Informatics, 75, S138-S148.
Cheng et al. Risk Prediction with Electronic Health Records: A Deep Learning Approach, May 2016, SIAM journal.†
Miotto et al., Deep Patient: an unsupervised representation to predict the future of patients from electronic health records. Scientific Reports, May 2016.†
Jagannatha et al., Structured prediction models for RNN based sequence labeling in clinical text, EMNLP, 2016.†
Pham et al., Predicting healthcare trajectories from medical records: A deep learning approach, Nov. 2016, Center for Pattern Recognition and Data Analytics, Deakin University, Australia.†
Evans et al., Automated identification and predictive tools to help identify high-risk heart failure patients: pilot evaluation, Journal of American Medical Informatics Association. (Sep. 2016).†
Miotto et al.; Deep Patient: An Unsupervised Representation to Predict the Future of Patients from Electronic Health Records; pp. 4, 5,8; Published May 17, 2016.†

\* cited by examiner
† cited by third party

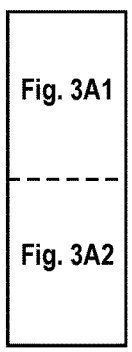
Fig. 3A
Fig. 3A1
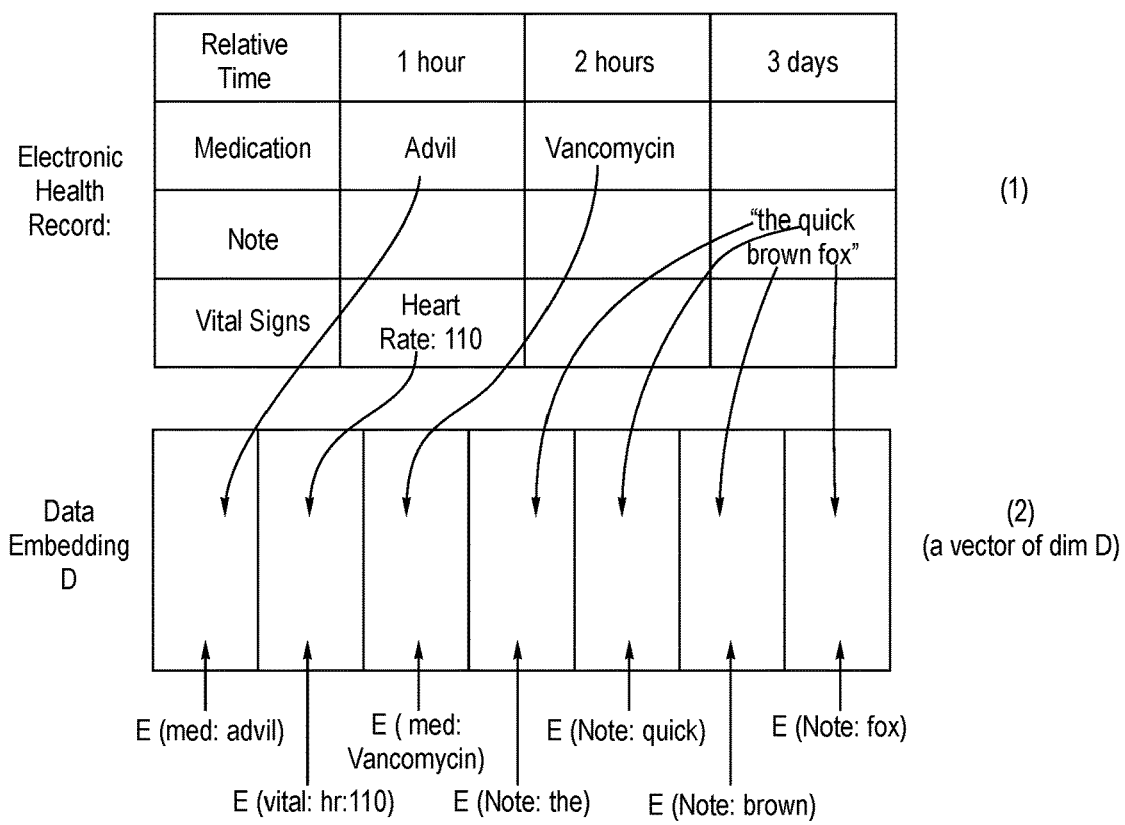
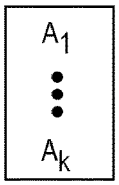
Bank of Predefined or Learned Functions

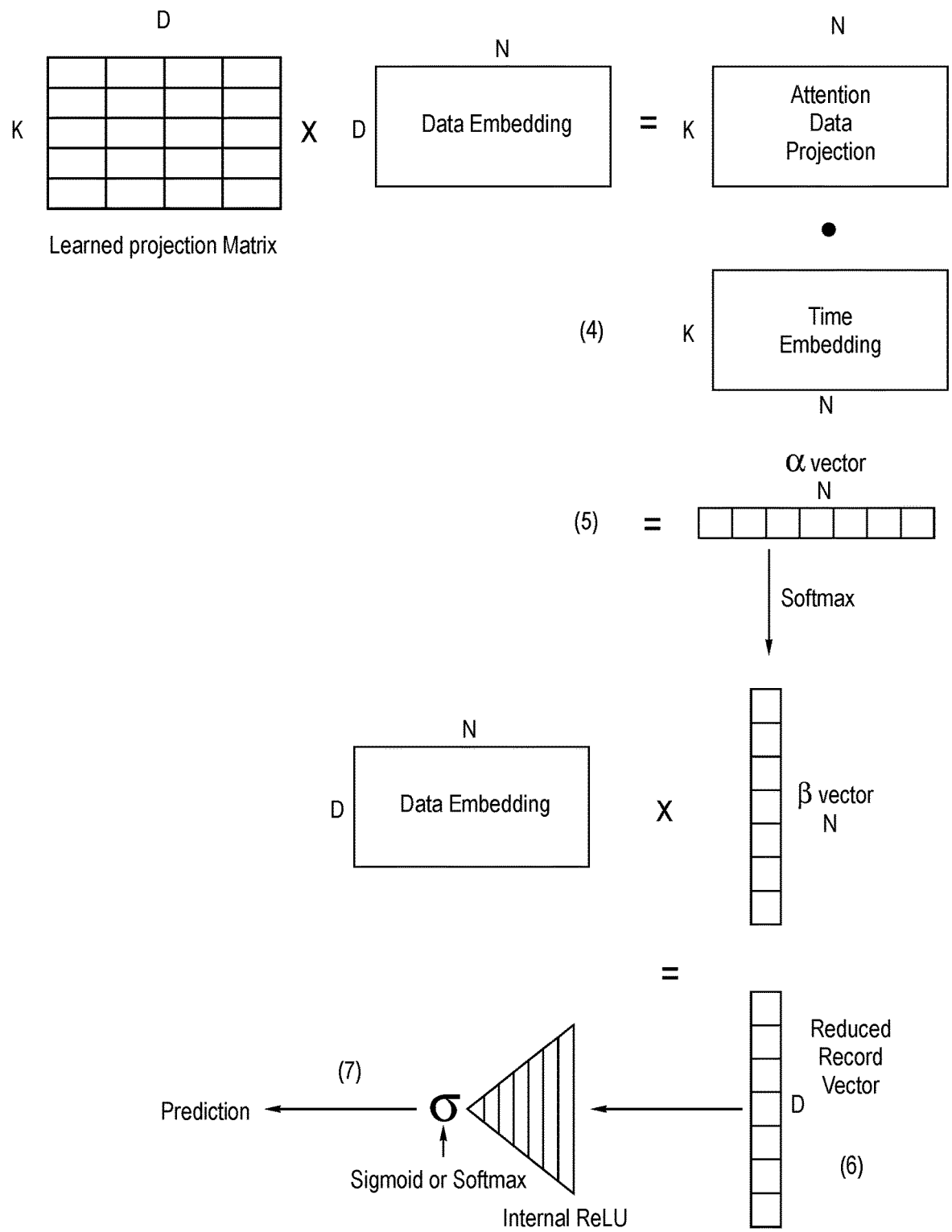
Fig. 3A2

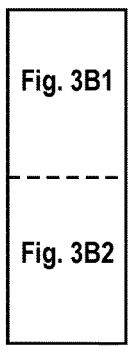

Electronic Health Record:

| Relative Time | 1 hour | 2 hours | 3 days |
|---|---|---|---|
| Medication | Advil | Vancomycin | |
| Note | | | "the quick brown fox" |
| Vital Signs | Heart Rate: 110 | | |

(1) ...

| 1 | 0 | 0 | 1 | 0 | ... | |
|---|---|---|---|---|---|---|
| $f_0$ | $f_1$ | $f_2$ | | | | $f_N$ |

(2) N-bit vector embedding $f_0$ : was heart rate $\geq$ 110 at time window $\leq$ 7 days? $\begin{array}{l}Y = 1\\N = 0\end{array}$ $f_1$ : did not contain "quick" at time window $\leq$ 7 days? $\begin{array}{l}Y = 1\\N = 0\end{array}$

V

| | | | | ... | |
|---|---|---|---|---|---|
| $t_0$ | $t_1$ | $t_2$ | | | $t_N$ |

*

E

| | | | | ... | |
|---|---|---|---|---|---|
| = | | | | ... | |
| = | | | | | |

Embedding Vector Dimension D

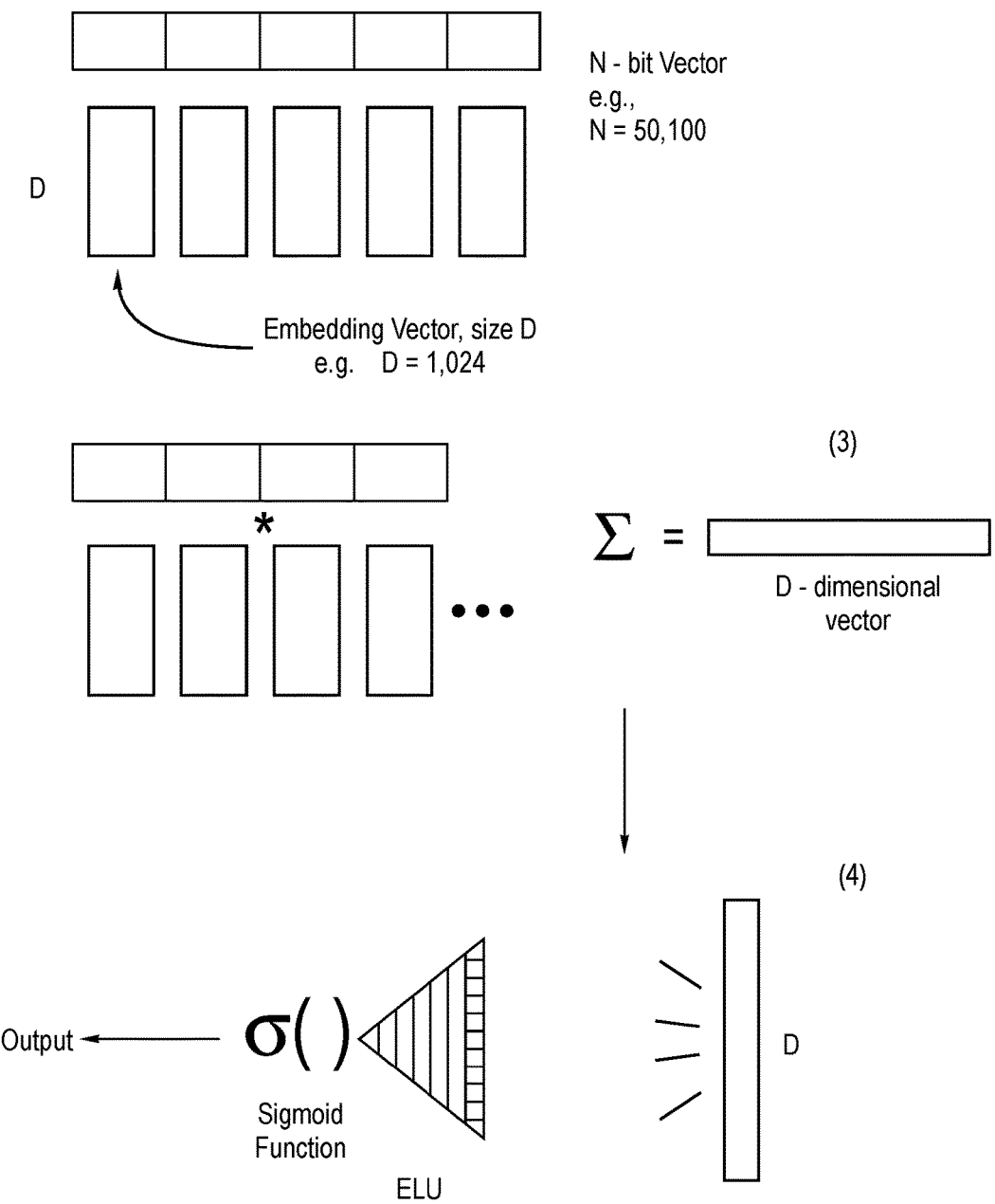
Fig. 3B2

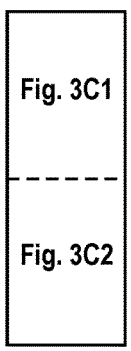
Fig. 3C
Fig. 3C1
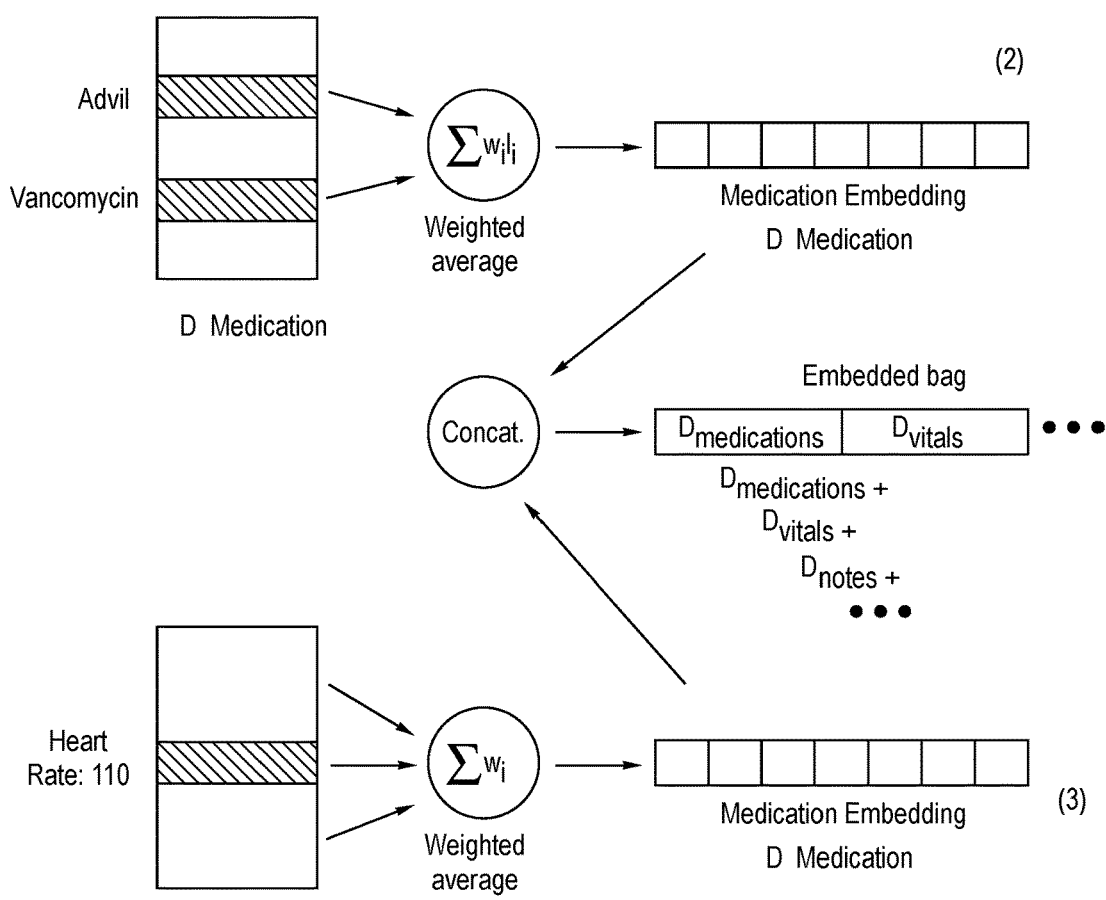

Fig. 3C2
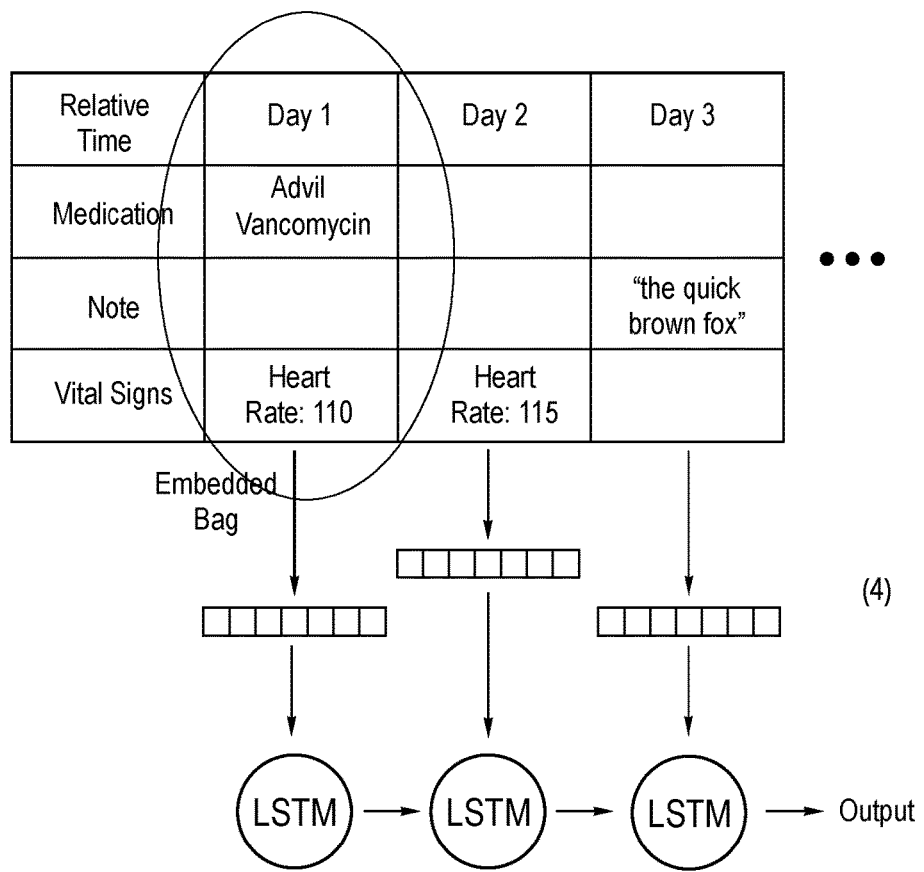

Fig. 5

Metastatic melanoma with pneumonia and anemia

Patient is a 66 y o male with *metatastic* MELANOMA on *chemotherapy*. Presenting with hemoptysis cta concerning for widespread METASTATIC disease *encasement* of pulmonary vein leading to hemoptysis and obstruction of rll bronchus leading to *postobstructive pna.*

Fig. 6

Alcohol-related disorder

53 year old woman with history of etoh *abuse* depression and htn presenting with etoh *abuse* and transferred to icu for etoh *withdrawal*. Was treated with valium per ciwa. Etoh *withdrawal heavy drinker* recent increased use, and experiencing *withdrawal* Discharged with outpatient psy f/u.

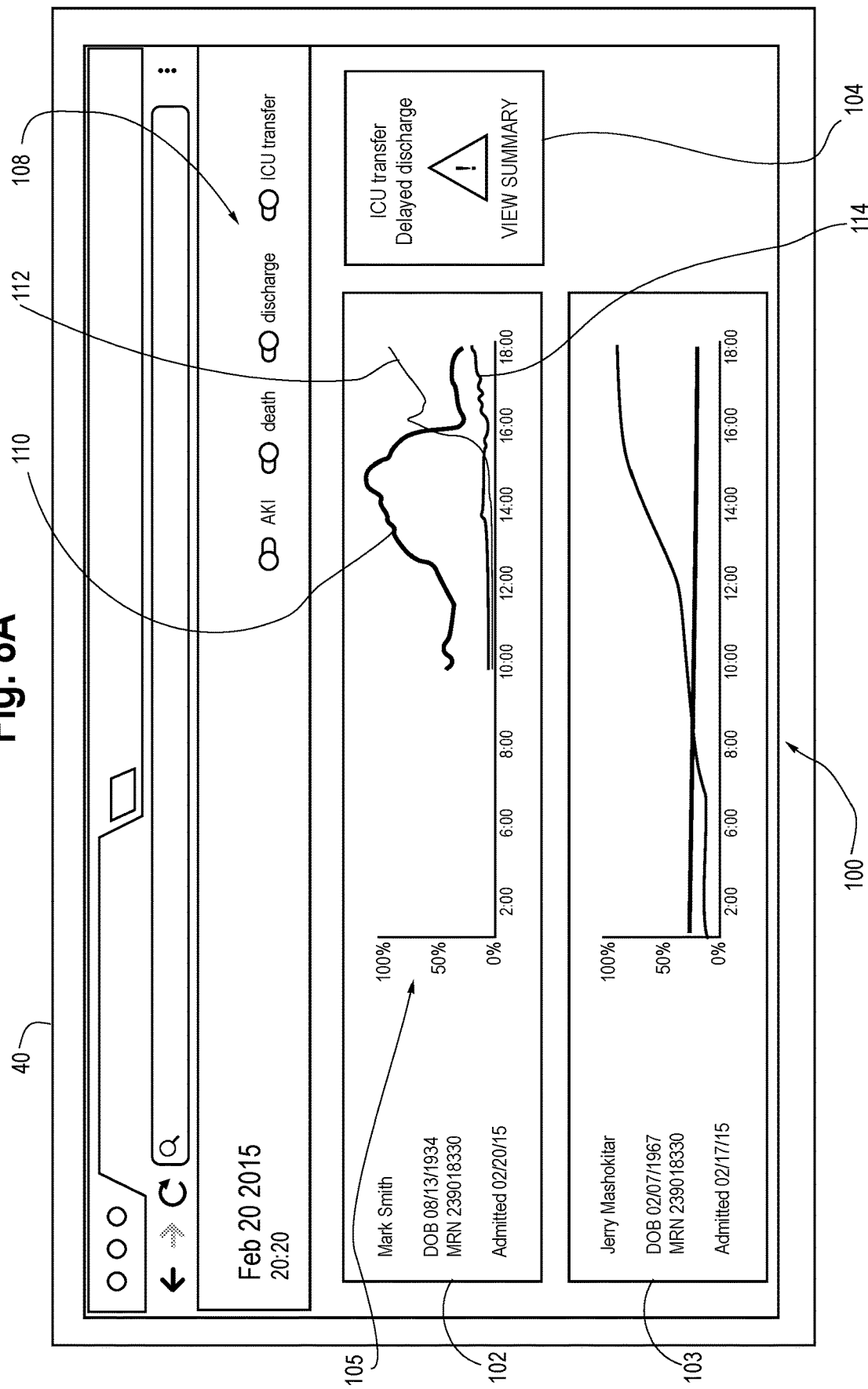

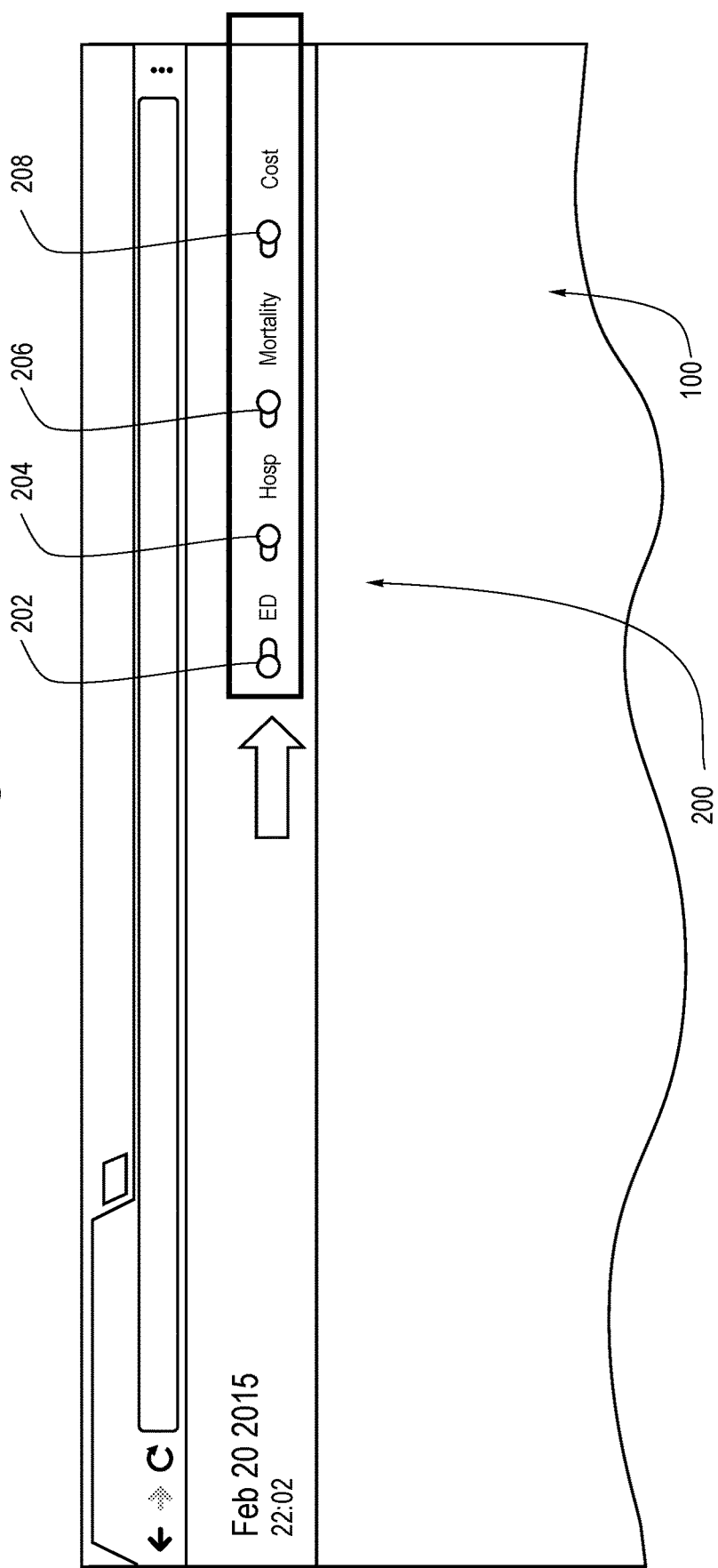

Fig. 10

What diseases does this patient have?

| Day | ICD code |
|---|---|
| day 0 | 278.0 |
| day 0 | V72.60 |
| day 0 | 195.0 |
| day 0 | 195.0 |
| day 0 | V58.69 |
| day 0 | 585.6 |
| day 0 | 311.0 |
| day 0 | 250.0 |
| day 0 | 401.1 |
| day 0 | 174.9 |
| day 0 | 327.2 |
| day 0 | 230.0 |
| day 0 | 185.0 |
| day 0 | V04.81 |
| day 0 | 729.5 |
| day 340 | 110 |
| day 340 | 174.9 |
| day 340 | 427.3 |
| day 340 | V58.11 |
| day 340 | 724.2 |
| day 340 | V58.11 |
| day 340 | 786.2 |
| day 340 | 724.2 |
| day 340 | 244.9 |
| day 340 | 244.9 |
| day 340 | 585.9 |
| day 340 | 585.9 |
| day 418 | 784.0 |
| day 418 | V58.11 |
| day 418 | 401.1 |
| day 418 | 110 |
| day 418 | V15.82 |
| day 418 | 285.9 |
| day 418 | 278.0 |
| day 418 | 453.9 |
| day 418 | 786.1 |
| day 418 | 784.0 |
| day 418 | 493.9 |

| Day | ICD code |
|---|---|
| day 424 | 244.9 |
| day 424 | 585.9 |
| day 430 | 185.0 |
| day 435 | V04.81 |
| day 435 | V64.2 |
| day 437 | V64.2 |
| day 437 | 203.0 |
| day 437 | 250.0 |
| day 437 | 719.4 |
| day 451 | 724.2 |
| day 451 | V70.5 |
| day 451 | V72.31 |
| day 451 | 427.3 |
| day 451 | 414.0 |
| day 451 | V10.3 |
| day 515 | 162.9 |
| day 515 | 414.0 |
| day 515 | V15.82 |
| day 515 | 401.1 |
| day 515 | V72.31 |
| day 515 | 786.2 |
| day 515 | 185.0 |
| day 681 | 185.0 |
| day 681 | 401.1 |
| day 681 | 278.0 |
| day 681 | 174.9 |
| day 681 | 174.9 |
| day 681 | V70.5 |
| day 681 | V64.2 |
| day 681 | V58.11 |
| day 681 | 174.9 |
| day 681 | 784.0 |
| day 681 | 719.5 |
| day 681 | 780.8 |
| day 681 | 272.0 |
| day 681 | 530.8 |
| day 681 | V04.81 |
| day 893 | 784.0 |

| Day | ICD code |
|---|---|
| day 893 | 203.0 |
| day 893 | 401.1 |
| day 893 | V72.60 |
| day 893 | 427.3 |
| day 893 | 272.4 |
| day 908 | 250.0 |
| day 1067 | V72.31 |
| day 1067 | 311.0 |
| day 1067 | 585.9 |
| day 1067 | 789.0 |
| day 1067 | 784.0 |
| day 1067 | 174.8 |
| day 1067 | 278.0 |
| day 1067 | V15.82 |
| day 1067 | 530.8 |
| day 1067 | V58.11 |
| day 1067 | 585.6 |
| day 1067 | 110 |
| day 1067 | V58.61 |
| day 1067 | V58.69 |
| day 1067 | 272.4 |
| day 1067 | 278.0 |
| day 1076 | 195.0 |
| day 1076 | 428.0 |
| day 1076 | 585.9 |
| day 1076 | 789.0 |
| day 1076 | 496.0 |
| day 1076 | 272.4 |
| day 1076 | 185.0 |
| day 1076 | V58.61 |
| day 1076 | V70.5 |
| day 1076 | V10.3 |
| day 1076 | 278.0 |
| day 1076 | V70.5 |
| day 1076 | 162.9 |
| day 1076 | V15.82 |
| day 1076 | 401.1 |
| day 1076 | V15.82 |

| Day | ICD code |
|---|---|
| day 1076 | 285.9 |
| day 1076 | 162.9 |
| day 1076 | V58.11 |
| day 1076 | 719.4 |
| day 1090 | 786.1 |
| day 1090 | V64.2 |
| day 1090 | 427.3 |
| day 1090 | 427.3 |
| day 1095 | 786.2 |
| day 1170 | V76.12 |
| day 1170 | 414.0 |
| day 1170 | 585.9 |
| day 1170 | 272.4 |
| day 1170 | V72.60 |
| day 1170 | 311.0 |
| day 1170 | 244.9 |
| day 1170 | 786.1 |
| day 1170 | 428.0 |
| day 1170 | 427.3 |
| day 1170 | 174.9 |
| day 1170 | 786.5 |
| day 1170 | V58.11 |
| day 1170 | V58.69 |
| day 1170 | 401.1 |
| day 1170 | V72.60 |
| day 1170 | 414.0 |
| day 1170 | 78602 |
| day 1170 | 719.4 |
| day 1170 | 784.0 |
| day 1170 | V64.2 |
| day 1184 | 724.2 |
| day 1184 | 185.0 |
| day 1185 | 585.9 |
| day 1201 | 414.0 |
| day 1201 | V70.5 |
| day 1201 | 719.5 |
| day 1201 | V64.2 |
| day 1201 | 786.5 |

1 patient
4 years of history
400+ listed diagnosis codes

Fig. 11

How do I tell if a disease if particularly severe?

| Day | ICD code |
|---|---|
| day 0 | 278.0 |
| day 0 | V72.60 |
| day 0 | 195.0 |
| day 0 | 195.0 |
| day 0 | V58.69 |
| day 0 | 585.6 |
| day 0 | 311.0 |
| day 0 | 250.0 |
| day 0 | 401.1 |
| day 0 | 174.9 |
| day 0 | 327.2 |
| day 0 | 230.0 |
| day 0 | 185.0 |
| day 0 | V04.81 |
| day 0 | 729.5 |
| day 340 | 110 |
| day 340 | 174.9 |
| day 340 | 427.3 |
| day 340 | V58.11 |
| day 340 | 724.2 |
| day 340 | V58.11 |
| day 340 | 786.2 |
| day 340 | 724.2 |
| day 340 | 244.9 |
| day 340 | 244.9 |
| day 340 | 585.9 |
| day 340 | 585.9 |
| day 418 | 784.0 |
| day 418 | V58.11 |
| day 418 | 401.1 |
| day 418 | 110 |
| day 418 | V15.82 |
| day 418 | 285.9 |
| day 418 | 278.0 |
| day 418 | 453.9 |
| day 418 | 786.1 |
| day 418 | 784.0 |
| day 418 | 493.9 |

| Day | ICD code |
|---|---|
| day 424 | 244.9 |
| day 424 | 585.9 |
| day 430 | 185.0 |
| day 435 | V04.81 |
| day 435 | V64.2 |
| day 437 | V64.2 |
| day 437 | 203.0 |
| day 437 | 250.0 |
| day 437 | 719.4 |
| day 451 | 724.2 |
| day 451 | V70.5 |
| day 451 | V72.31 |
| day 451 | 427.3 |
| day 451 | 414.0 |
| day 451 | V10.3 |
| day 515 | 162.9 |
| day 515 | 414.0 |
| day 515 | V15.82 |
| day 515 | 401.1 |
| day 515 | V72.31 |
| day 515 | 786.2 |
| day 515 | 185.0 |
| day 681 | 185.0 |
| day 681 | 401.1 |
| day 681 | 278.0 |
| day 681 | 174.9 |
| day 681 | 174.9 |
| day 681 | V70.5 |
| day 681 | V64.2 |
| day 681 | V58.11 |
| day 681 | 174.9 |
| day 681 | 784.0 |
| day 681 | 719.5 |
| day 681 | 780.8 |
| day 681 | 272.0 |
| day 681 | 530.8 |
| day 681 | V04.81 |
| day 893 | 784.0 |

| Day | ICD code |
|---|---|
| day 893 | 203.0 |
| day 893 | 401.1 |
| day 893 | V72.60 |
| day 893 | 427.3 |
| day 893 | 272.4 |
| day 908 | 250.0 |
| day 1067 | V72.31 |
| day 1067 | 311.0 |
| day 1067 | 585.9 |
| day 1067 | 789.0 |
| day 1067 | 784.0 |
| day 1067 | 174.8 |
| day 1067 | 278.0 |
| day 1067 | V15.82 |
| day 1067 | 530.8 |
| day 1067 | V58.11 |
| day 1067 | 585.6 |
| day 1067 | 110 |
| day 1067 | V58.61 |
| day 1067 | V58.69 |
| day 1067 | 272.4 |
| day 1067 | 278.0 |
| day 1076 | 195.0 |
| day 1076 | 428.0 |
| day 1076 | 585.9 |
| day 1076 | 789.0 |
| day 1076 | 496.0 |
| day 1076 | 272.4 |
| day 1076 | 185.0 |
| day 1076 | V58.61 |
| day 1076 | V70.5 |
| day 1076 | V10.3 |
| day 1076 | 278.0 |
| day 1076 | V70.5 |
| day 1076 | 162.9 |
| day 1076 | V15.82 |
| day 1076 | 401.1 |
| day 1076 | V15.82 |

| Day | ICD code |
|---|---|
| day 1076 | 285.9 |
| day 1076 | 162.9 |
| day 1076 | V58.11 |
| day 1076 | 719.4 |
| day 1090 | 786.1 |
| day 1090 | V64.2 |
| day 1090 | 427.3 |
| day 1095 | 427.3 |
| day 1170 | 786.2 |
| day 1170 | V76.12 |
| day 1170 | 414.0 |
| day 1170 | 585.9 |
| day 1170 | 272.4 |
| day 1170 | V72.60 |
| day 1170 | 311.0 |
| day 1170 | 244.9 |
| day 1170 | 786.1 |
| day 1170 | 428.0 |
| day 1170 | 427.3 |
| day 1170 | 174.9 |
| day 1170 | 786.5 |
| day 1170 | V58.11 |
| day 1170 | V58.69 |
| day 1170 | 401.1 |
| day 1170 | V72.60 |
| day 1170 | 414.0 |
| day 1170 | 78602 |
| day 1170 | 719.4 |
| day 1170 | 784.0 |
| day 1170 | V64.2 |
| day 1184 | 724.2 |
| day 1184 | 185.0 |
| day 1185 | 585.9 |
| day 1201 | 414.0 |
| day 1201 | V70.5 |
| day 1201 | 719.5 |
| day 1201 | V64.2 |
| day 1201 | 786.5 |

Were these treated as an outpatient, inpatient, ICU?

Fig. 12

What happened in all of these encounters?

| Day | type | | Day | type | | Day | type | | Day | type |
|---|---|---|---|---|---|---|---|---|---|---|
| day 1 | Office visit | | day 91 | Office visit | | day 160 | Administrative | | day 192 | Phone call |
| day 1 | Administrative | | day 91 | Hospital visit | | day 162 | Phone call | | day 193 | Administrative |
| day 2 | Hospital visit | | day 92 | Phone call | | day 162 | Hospital visit | | day 193 | Administrative |
| day 33 | Hospital visit | | day 92 | Phone call | | day 163 | Phone call | | day 194 | Office visit |
| day 35 | Administrative | | day 92 | Administrative | | day 164 | Orders | | day 195 | Phone call |
| day 35 | Office visit | | day 93 | Surgery | | day 164 | Office visit | | day 196 | Administrative |
| day 49 | Office visit | | day 93 | Administrative | | day 165 | Office visit | | day 198 | Phone call |
| day 55 | Administrative | | day 94 | Anesthesia | | day 165 | Phone call | | day 199 | Administrative |
| day 57 | Office visit | | day 94 | Anesthesia | | day 165 | Orders | | day 200 | Office visit |
| day 58 | 1Administrative | | day 95 | Hospital visit | | day 166 | Hospital visit | | day 201 | Hospital visit |
| day 58 | Administrative | | day 95 | Office visit | | day 169 | Administrative | | day 203 | Administrative |
| day 59 | Phone call | | day 97 | Office visit | | day 172 | Phone call | | day 203 | Administrative |
| day 61 | Anesthesia | | day 100 | Office visit | | day 172 | Orders | | day 204 | Office visit |
| day 62 | Surgery | | day 102 | Phone call | | day 172 | Phone call | | day 208 | Administrative |
| day 63 | Anesthesia | | day 105 | Phone call | | day 172 | Hospital visit | | day 208 | Office visit |
| day 63 | Administrative | | day 107 | Phone call | | day 173 | Hospital visit | | day 218 | Phone call |
| day 63 | Phone call | | day 108 | Phone call | | day 174 | Surgery | | day 225 | Administrative |
| day 64 | Administrative | | day 110 | Administrative | | day 174 | Anesthesia | | day 226 | Hospital visit |
| day 64 | Office visit | | day 110 | Phone call | | day 175 | Anesthesia | | day 226 | Office visit |
| day 66 | Office visit | | day 112 | Administrative | | day 175 | Administrative | | day 231 | Letter |
| day 67 | Office visit | | day 115 | Office visit | | day 176 | Orders | | day 233 | Hospital visit |
| day 68 | Administrative | | day 117 | Phone call | | day 177 | Phone call | | day 233 | Phone call |
| day 75 | Administrative | | day 119 | Orders | | day 177 | Phone call | | day 235 | Administrative |
| day 76 | Administrative | | day 123 | Office visit | | day 179 | Office visit | | day 235 | Office visit |
| day 76 | Office visit | | day 124 | Administrative | | day 182 | Anesthesia | | day 237 | Phone call |
| day 76 | Office visit | | day 126 | Phone call | | day 184 | Phone call | | day 237 | Administrative |
| day 79 | Administrative | | day 132 | Hospital visit | | day 184 | Anesthesia | | day 238 | Office visit |
| day 79 | Phone call | | day 132 | Phone call | | day 185 | Phone call | | day 238 | Hospital visit |
| day 79 | Administrative | | day 133 | Office visit | | day 185 | Hospital visit | | day 239 | Phone call |
| day 81 | Hospital visit | | day 133 | Administrative | | day 185 | Administrative | | day 243 | Phone call |
| day 81 | Administrative | | day 135 | Phone call | | day 185 | Surgery | | day 245 | Office visit |
| day 82 | Office visit | | day 139 | Administrative | | day 187 | Office visit | | day 245 | Administrative |
| day 82 | Phone call | | day 141 | Office visit | | day 187 | Hospital visit | | day 251 | Orders |
| day 83 | Hospital visit | | day 142 | Phone call | | day 188 | Office visit | | day 251 | Administrative |
| day 84 | Administrative | | day 147 | Administrative | | day 188 | Administrative | | day 259 | Phone call |
| day 88 | Administrative | | day 152 | Administrative | | day 189 | Office visit | | day 266 | Office visit |
| day 89 | Administrative | | day 152 | Office visit | | day 190 | Administrative | | day 289 | Office visit |
| day 89 | Administrative | | day 153 | Administrative | | | | | day 305 | Office visit |

1 patient
150+ encounters
What happened?

Guardian shows an enhanced problem list

Guardian can summarize each medical problem: alcohol withdrawal

Guardian can summarize each medical problem: cardiomyopathy

SYSTEM AND METHOD FOR PREDICTING AND SUMMARIZING MEDICAL EVENTS FROM ELECTRONIC HEALTH RECORDS

PRIORITY

This application claims priority benefits under 35 U.S.C. § 119 to U.S. provisional application Ser. No. 62/538,112 filed Jul. 28, 2017. The entire content of the '112 provisional application, including Appendices A and B, is incorporated by reference herein.

BACKGROUND

This disclosure is directed to a system and method for predicting and summarizing medical events from electronic health records using deep learning models. The disclosure is also directed to several component aspects and combinations thereof, including consolidation of electronic health records into a single format for model generation and training, deep learning models for predicting health events from medical records, and a provider-facing interface on an electronic device for display of clinical predictions and underlying pertinent medical events relevant to the predictions obtained through deep learning.

Nobel Laureate Herbert Simon once said: "What information consumes is rather obvious: it consumes the attention of its recipients. Hence a wealth of information creates a poverty of attention ... and a need to allocate that attention efficiently among the overabundance of information sources that might consume it." In the clinical setting, the management and presentation of information regarding a patient is an important aspect of patient care and healthcare decision making, for example how to treat a patient or when to discharge a patient from a hospital. Management of information is a particularly acute issue in a busy hospital or clinic situation where a healthcare provider, such as a nurse or physician, is attending to many patients simultaneously. Information, for example, contained within the electronic health records of a patient, consumes the attention of the recipient (e.g., nurse or physician). A wealth of information, for example as contained in an extensive medical history for a particular patient over many years, or more usually the medical history of a multitude of patients, creates a poverty of attention.

There is a need for systems and methods to assist healthcare providers to allocate their attention efficiently among the overabundance of information from diverse sources, as well as to provide predictions of future clinical events and highlighting of relevant underlying medical events contributing to these predictions in a timely manner. The present disclosure address a pressing question facing the physician in the hospital, namely which patients have the highest need for my attention now and, at an individual level, what information in the patient's chart should I attend to?

RELATED ART

The rapid adoption of electronic health records (EHRs) has made routine clinical data digitally abundant. Adler-Milstein J, DesRoches C M, Kralovec P, et al. *Electronic Health Record Adoption In US Hospitals: Progress Continues, But Challenges Persist*. Health Aff. 2015; 34(12):2174-2180. Henry J, et al., *Adoption of Electronic Health Record Systems among U.S. Non-Federal Acute Care Hospitals: 2008-2015*, Office of the National Coordinator for Health Information Technology, ONC data brief no. 35, May 2016. This phenomenon has spurred efforts to harness it with algorithms to target interventions at patients predicted to be at high risk for readmission, see Parikh R B, Kakad M, Bates D W. *Integrating Predictive Analytics Into High-Value Care: The Dawn of Precision Delivery*. JAMA. 2016; 315(7):651-652, triage patients at risk for adverse events or decompensation, see Bates D W, Saria S, Ohno-Machado L, Shah A, Escobar G. *Big data in healthcare: using analytics to identify and manage high-risk and high-cost patients*. Health Aff. 2014; 33(7):1123-1131; Obermeyer Z, Emanuel E J. *Predicting the Future—Big Data, Machine Learning, and Clinical Medicine*. N Engl J Med. 2016; 375(13):1216-1219, and even recommend specific cancer treatments. See Kantarjian H, Yu P P. *Artificial Intelligence, Big Data, and Cancer*. JAMA Oncol. 2015; 1(5):573-574.

Traditionally, these predictive models are created separately for each task by collecting variables that are measured consistently on a pre-specified cohort, often in a clinical registry or trial to ensure high-quality data collection. By contrast, data generated in routine care may produce datasets that are incomplete, inaccurate, and inconsistent. Hersh W R, Weiner M G, Embi P J, et al. *Caveats for the use of operational electronic health record data in comparative effectiveness research*. Med Care. 2013; 51(8 Suppl 3):S30-S37; Newton K M, Peissig P L, Kho A N, et al. *Validation of electronic medical record-based phenotyping algorithms: results and lessons learned from the eMERGE network*. J Am Med Inform Assoc. 2013; 20(e1):e147-e154; Opmeer B C. *Electronic Health Records as Sources of Research Data*. JAMA. 2016; 315(2):201-202. Therefore, to create a predictive model, researchers expend considerable effort to define variables, normalize data, and handle missing measurements (see e.g., the Newton and Opmeer references) which complicates deployment as such steps must be recreated, in real-time, on live data. Goldstein B A, Navar A M, Pencina M J, Ioannidis J P A. Opportunities and challenges in developing risk prediction models with electronic health records data: a systematic review. J Am Med Inform Assoc. 2017; 24(1):198-208. Given the above, the median number of variables in predictive models is 27, see Goldstein et al., supra, thus ignoring most data, especially unstructured data like notes, and repeated measurements like vital signs and lab results.

SUMMARY

As an overview and summary, one aspect of this disclosure is directed to a system for predicting and summarizing medical events from electronic health records. The system includes three components:

First, the system includes a computer memory, e.g. mass data storage device or devices, storing aggregated electronic health records from a multitude (e.g., millions) of patients of diverse age, health conditions, and demographics, the records including among other things medications, laboratory values, diagnoses, vital signs, and medical notes, i.e., free text entered by a provider. The aggregated health records are patient de-identified and obtained from one or more sources and are potentially organized in different data structure types due to differences in legacy systems. The aggregated electronic health records are converted into a single standardized data structure format and preferably placed in an ordered format, such as for example a chronological order.

Secondly, the system includes a computer (the term is intended to refer to a single computer or a system of computers or processing units sharing a processing task, including ancillary memory) executing one or more machine learning models trained on the aggregated health records converted into the standardized data structure format and in the ordered format. The deep learning models are trained to predict one or more future clinical events and to summarize or highlight pertinent past medical events (e.g., diagnoses, medications, notes or excerpts thereof) related to the predicted one or more future clinical events, on an input electronic health record of a given patient. The input electronic health record is in the standardized data structure format and ordered into a chronological order, as is the case with the aggregated health records used for model training.

Thirdly, the system includes an electronic device for use by a healthcare provider treating the patient, e.g., a computer terminal or workstation, tablet, smartphone or other type of computing device having a screen display, which is configured with a client-facing interface displaying the predicted one or more future clinical events and the pertinent past medical events of the patient generated by the one or more predictive models.

In the detailed description, we describe that the aggregated health records may take the form of health records from a multitude of patients (hundreds of thousands or even millions of patients) obtained in a de-identified form from a plurality of different institutions, e.g., hospitals or medical systems. The data from the different institutions may be in different data formats, due to lack of standardization in the industry. The records are converted into the standardized data structure format. In one embodiment they are arranged in time sequence on a per-patient basis. There is de-identification of the patient in the aggregated health records. In one particular embodiment, the standardized data structure format is the Fast Health Interoperability Resources (FHIR) format, a known format, see Mandel J C, et al., *SMART on FHIR: a standards-based, interoperable apps platform for electronic health records*. J Am Med Inform Assoc. 2016; 23(5):899-908, in which the EHRs are formatted in bundles of time-sequenced FHIR "resources."

In one embodiment, the aggregated health records contain variable names which are not harmonized to a standard terminology, except for variables that are required to define primary outcomes and exclusion criteria, i.e., criteria for excluding a given EHR from being included for model training. In one embodiment, the aggregated health records contain hospitalization diagnoses, and the diagnoses are mapped to single-level Clinical Classification Software (CCS) codes.

In one aspect, one or more of the deep learning models contain "attention mechanisms" (a technique known in the field of deep learning and described in detail below, also sometimes referred to as "attribution mechanisms") which, when invoked, indicate how much attention or equivalently "weight" the one or more models gave to particular "tokens" corresponding to atomic elements (individual words in a note, lab measurements, medications, etc.) in the electronic health record in order to arrive at the prediction of the one or more future clinical events and pertinent past medical events. The provider-facing interface preferably includes a display of the results of the attention mechanism, such as by providing degrees of highlighting or emphasis on elements in the health record (i.e., past medical events) associated with a particular prediction, especially those that scored high from the attention mechanism. The display of the results of the attention mechanism on the electronic device, in addition to the prediction and related medical events, provides the healthcare provider with confidence in the prediction and its basis, and directs their attention to pertinent elements or features of the health record related to the prediction to inform and guide their patient care.

Aspects of this disclosure are directed to deep learning models which are used to make the predictions. In one embodiment, we contemplate using an ensemble of deep learning neural network models, each of which are individually trained on the aggregated EHRs. In one embodiment we use (1) a Long-Short-Term Memory (LSTM) model, (2) a time aware Feed-Forward Model (FFM), also referred to herein as a feedforward model with Time-Aware Attention, and (3) an embedded boosted time-series model, also referred to herein as an Embedded Time-Aware Boosting model. Alternatives to these models may be suitable for use in the present system, such as, for example autoregressive convolutional neural network models with attention, see A. Vaswani et al., Attention is all you need, arXiv:1706.03762 [cs.CL] (June 2017). The predictions of one or more future clinical events and summarized pertinent past medical events related to the predicted one or more future clinical events can be obtained from an ensemble average of the three deep learning models. In some instances the prediction from a member of the ensemble may be excluded, for various reasons.

We disclose a variety of possible predictions of future clinical events, and in one embodiment the deep learning model(s) predicts at least one of unplanned transfer to intensive care unit, length of stay in a hospital greater than 7 days, unplanned hospitalization, ER visit or readmission within 30 days after discharge of the patient, inpatient mortality, primary diagnosis, or a complete set of primary and secondary billing diagnoses at patient discharge. We also disclose the ability to predict atypical laboratory values, including potentially things such as acute kidney injury, hypokalemia, hypoglycemia, or hyponeutrimia. We describe below still further additional prediction tasks that the models can be used for.

Further aspects of the present disclosure are directed to the electronic device and its provider-facing interface. In one embodiment, the interface includes a display of: (1) an alert to the predicted one or more future clinical events, (2) key medical problems or conditions (i.e., past medical events) related to the alert, and (3) notes or excerpts thereof, e.g., words or phrases, related to the alert. In one configuration, the deep learning models contain an attention mechanism indicating how much attention the one or more models gave to tokens corresponding to elements in the electronic health record to predict the one or more future clinical events. The display of the notes or excerpts thereof are displayed in a manner indicating results from the application of the attention mechanism, e.g., by the use of highlighting or degrees of emphasis on particular words, phrases or other text in the notes, e.g., by varying font size, color, shading, bold, italics, underline, strikethough, blinking, highlighting, font selection, etc., thereby drawing the attention of the provider to the most significant past medical events in the EHR that are pertinent to the predicted future clinical event. In still one further configuration, the display can further include inferred information from the patient electronic health record (e.g., a tentative diagnosis inferred from past medical events) and a timeline or plot of risk or probability of certain clinical events occurring in the future, such as death or transfer to the ICU.

In one possible configuration, the display permits a user of the electronic device to select one of the key problems or conditions and the selection triggers further display of information pertinent to the selected key problem or condition, for example display of medications prescribed to the patient and notes or excerpts thereof related to the selected key problem or condition.

In another aspect, this disclosure is directed to a system which includes:

a) computer memory storing aggregated electronic health records from a multitude of patients of diverse age, health conditions, and demographics including some or all of medications, laboratory values, diagnoses, vital signs, and medical notes, and obtained in different formats, wherein the aggregated electronic health records are converted into a single standardized data structure format and ordered per patient into an ordered arrangement; and b) a computer executing one or more deep learning models trained on the aggregated health records converted into the single standardized data structure format and in the ordered arrangement to predict future clinical events on an input electronic health record of a patient.

In one embodiment, the aggregated health records are in the form of health records arranged in different data formats. The standardized data structure format may take the form of Fast Health Interoperability Resources (FHIR). The aggregated health records contain variable names which are not harmonized to a standard terminology except for variables required to define primary outcomes and exclusion criteria. The aggregated health records may contain hospitalization diagnoses, and the diagnoses are mapped to single-level Clinical Classification Software (CCS) codes. In one embodiment, wherein the electronic health records are ordered per patient into a chronological order.

In another aspect, a method is disclosed for generating training data for machine learning from a set of raw electronic health records of a multitude of patients from diverse sources in diverse data formats. The method includes the steps of:

a) obtaining the set of raw electronic health records;

b) converting the set of raw electronic health records into a single standardized data structure format;

c) ordering the electronic health records converted into the single standardized data structure format into a time-sequenced order per patient; and d) storing the time-sequenced ordered electronic health records in the standardized data structure format in a data storage device.

The set of electronic health records can include both structured data and unstructured data including free text notes. In one embodiment the converting step b) is performed without harmonization of terminology in the raw electronic health records to a standard terminology.

In another aspect of the disclosure, a method is described for predicting and summarizing medical events from electronic health records. The method includes the steps of:

a) aggregating electronic health records from a multitude of patients of diverse age, health conditions, and demographics, the electronic health records including some or all of medications, laboratory values, diagnoses, vital signs, and medical notes;

b) converting the aggregated electronic health records into a single standardized data structure format and into an ordered arrangement per patient;

c) training one or more deep learning models on the aggregated health records converted into the single standardized data structure format and in the ordered arrangement;

d) using the trained one or more deep learning models to predict one or more future clinical events and summarize pertinent past medical events related to the predicted one or more future clinical events from an input electronic health record of a patient having the standardized data structure format and ordered into a chronological order; and e) generating data for a healthcare provider-facing interface of an electronic device for use by a healthcare provider displaying the predicted one or more future clinical events and the pertinent past medical events of the patient.

In still another aspect, a system is described comprising in combination:

a) computer memory storing aggregated electronic health records from a multitude of patients of diverse age, health conditions, and demographics including some or all of medications, laboratory values, diagnoses, vital signs, and medical notes, and obtained in different formats, wherein the aggregated electronic health records are converted into a single standardized data structure format and placed in an ordered arrangement, such as a chronological order; and b) a computer (as defined above) executing one or more deep learning models trained on the aggregated health records converted into the single standardized data structure format and in ordered arrangement to predict future clinical events on an input electronic health record of a patient. In one aspect, the one or more deep learning models each contain "attention mechanisms" indicating how much attention the one or more models give to particular "tokens" corresponding to atomic elements (individual words in a note, lab measurements, medications, etc.) in the electronic health record in order to arrive at a prediction of the one or more future clinical events and summarize pertinent past medical events related to the predicted one or more future clinical events. In one embodiment, we contemplate using an ensemble of deep learning neural network models, each of which are individually trained on the aggregated EHRs. In one embodiment we use (1) a Long-Short-Term Memory (LSTM) model, (2) a time aware Feed-Forward Model (FFM), and (3) an embedded boosted time-series model.

In yet another aspect of this disclosure, a method for predicting medical events from electronic health records is described. The method includes the steps of:

a) aggregating electronic health records from a multitude of patients of diverse age, health conditions, and demographics, the electronic health records including some or all of medications, laboratory values, diagnoses, vital signs, and medical notes and obtained in different formats;

b) converting the aggregated electronic health records into a single standardized data structure format and ordered per patient into an ordered arrangement, such as for example a chronological order; and c) training one or more deep learning models on the aggregated health records converted into the single standardized data structure format and in ordered arrangement, wherein the trained one or more deep learning models predict future clinical events on an input electronic health record of a patient in the standardized data structure format and ordered in a chronological order.

In still another aspect, we have described an improved computer (as defined previously) executing one or more deep learning models trained on aggregated electronic health records converted into a single standardized data structure format and in the chronological order to predict one or more future clinical events and summarize pertinent past medical events related to the predicted one or more future clinical events on an input electronic health record of a patient having the standardized data structure format and ordered into a chronological order.

In a preferred embodiment the deep learning models each contain attention mechanisms indicating how attention the one or more models give to particular "tokens" corresponding to atomic elements (individual words in a note, lab measurements, medications, etc.) in the electronic health record elements in the electronic health record to predict the one or more future clinical events and summarize pertinent past medical events related to the predicted one or more future clinical events.

In still another aspect, a system is disclosed comprising, in combination, a) a computer executing one or more deep learning models trained on the aggregated health records converted into the single standardized data structure format and in the chronological order to predict one or more future clinical events and summarize pertinent past medical events related to the predicted one or more future clinical events on an input electronic health record of a patient having the standardized data structure format and ordered into a chronological order; and b) a client-facing interface of an electronic device for use by a healthcare provider treating the patient configured to display the predicted one or more future clinical events and the pertinent past medical events of the patient.

In yet another aspect, there is disclosed an electronic device (e.g., workstation, tablet computer or smartphone) having a healthcare provider facing interface displaying in substantial real time a display of a prediction of one or more future clinical events for at least one patient. The display further is configured to display elements (past medical events) from an electronic health record which correspond to application of an attention mechanism on a predictive model operating on the electronic health record which are related to the prediction. In one embodiment the elements of the electronic health record are notes or extracts thereof with highlighting or gradations of emphasis on particular words, phrases or other text in the notes. The elements of the electronic health record could also be things such as lab values, prior medications, vital signs, etc. The highlighting or gradations of emphasis could take the form of at least one of font size, font color, shading, bold, italics, underline, strikethough, blinking, highlighting with color, and font selection, or possibly some combination thereof, such as red color and bold font. The predicted one or more future clinical events could include unplanned transfer to intensive care unit, length of stay in a hospital greater than 7 days, unplanned readmission within 30 days after discharge of the patient, inpatient mortality, primary diagnosis, a complete set of primary and secondary billing diagnoses, or atypical laboratory values, such as acute kidney injury, hypokalemia, hypoglycemia, and hyponeutrimia.

In one embodiment, the interface is further configured to display a time line plotting at least one patient risk or probability over time, for example, a plot of risk of transfer to ICU or risk of hospital stay greater than 7 days, or risk of death. The electronic device could be used in a hospital or clinic environment in which the system is functioning to predict future clinical events for multiple patients simultaneously, in which case the interface is further configured to display a time line plotting at least one patient risk or probability over time for a plurality of patients simultaneously.

BRIEF DESCRIPTION OF THE DRAWINGS

FIG. 3A is a flow chart showing the design and operation of a time aware Feed Forward Model of FIG. 1; FIG. 3B is a flow chart showing the design and operation of an embedded boosted time series model of FIG. 1; FIG. 3C is a flow chart showing the design and operation of a LSTM model of FIG. 1.

FIG. 5 is an illustration of another form of display of data in an EHR showing results of attention mechanism in the deep learning models in the form of excerpts of notes with degrees of emphasis (size, boldness, color, etc.) given to individual words or phrases in the notes corresponding to the attention (significance or weight) the words were to a clinical prediction generated by the deep learning models, and attention particular medications in the medical history were to the prediction.

FIG. 6 is another example of results of the attention mechanism in the deep learning models, showing different words or phrases found in the notes of the EHR being afforded different degrees of emphasis (bold) being relevant to a prediction. The darker highlights correspond to higher attention scores.

FIG. 8A is an illustration of a healthcare provider-facing interface of an electronic device for use by a healthcare provider treating the patient, e.g., computer terminal, tablet, smartphone or other type of computing device having a screen display. The interface in this configuration is designed for use in a hospital setting, showing plots of risks for two patients simultaneously. The interface displays two predicted future clinical events for a particular patient, in this case an unplanned transfer to intensive care unit (ICU) and a delayed discharge from the hospital. The display of FIG. 8A is designed to alert the healthcare provider's attention early on to patients at risk.

FIG. 9 shows the display of tools on the interface that would be pertinent to use of the interface in predictions for outpatients.

FIGS. 10-13 illustrate hypothetical examples of the massive amount of information that is available to healthcare providers from EHRs and why the features of the present disclosure are needed. FIG. 10 shows excerpts from four years of a patient's medical history, with over 400 listed diagnoses. FIG. 11 shows excerpts of diagnoses for a patent, but the lack of important accompanying information such as whether the patient was treated as an outpatient, inpatient, or in the ICU or other setting. FIG. 12 shows over 150 different encounters for a particularly patient over a given time span, but lacks the detail on what happened in each encounter. FIG. 13 shows just one small fraction of the notes taken by providers in a single hypothetical four day hospitalization; the display of all of the notes would require 60 different screens of a standard mobile device.

In the figures and accompanying description all patient and provider names and medical data are fictitious and do not reveal any confidential patient information.

DETAILED DESCRIPTION

A. Overview

This disclosure describes a new method of configuring EHR data for use in training of predictive models. The models use all data recorded about patients, including clinical notes, variables in the raw unharmonized formats or terminologies, and preserve the temporal ordering of data collection. We further applied an aspect of deep learning to generate and train models to make clinical predictions from the EHR data. We chose deep learning because it handles millions of variables, can auto-harmonize data from different sources, and accommodates sequences of data with variable length. Deep learning techniques have achieved state-of-the-art performance in other complex domains like medical image recognition (e.g., to detect diabetic retinopathy and cancerous skin lesions), and language translation. Many of the applications and implementations of these deep learning models to the present problem domain are believed to be new.

This document further demonstrates the technical feasibility and clinical utility of our approach. We describe predictive models for multiple clinical tasks, including predicting hospital length-of-stay to improve throughput and reduce cost; predicting unplanned readmissions to target interventions to high-risk patients; predicting inpatient mortality to assist in deployment of early interventions; predicting and phenotyping diagnoses from routine clinical data to enable clinical decision support. Furthermore, we have described applications of the models to predict unplanned transfer of patients in a hospital to an intensive care unit, and primary diagnosis. Additionally, we describe a provider-facing user interface of an electronic device (e.g., computer terminal, tablet or smartphone) which presents these predictions and underlying relevant medical events that assist providers in treating patients in a timely manner.

Figure 1:
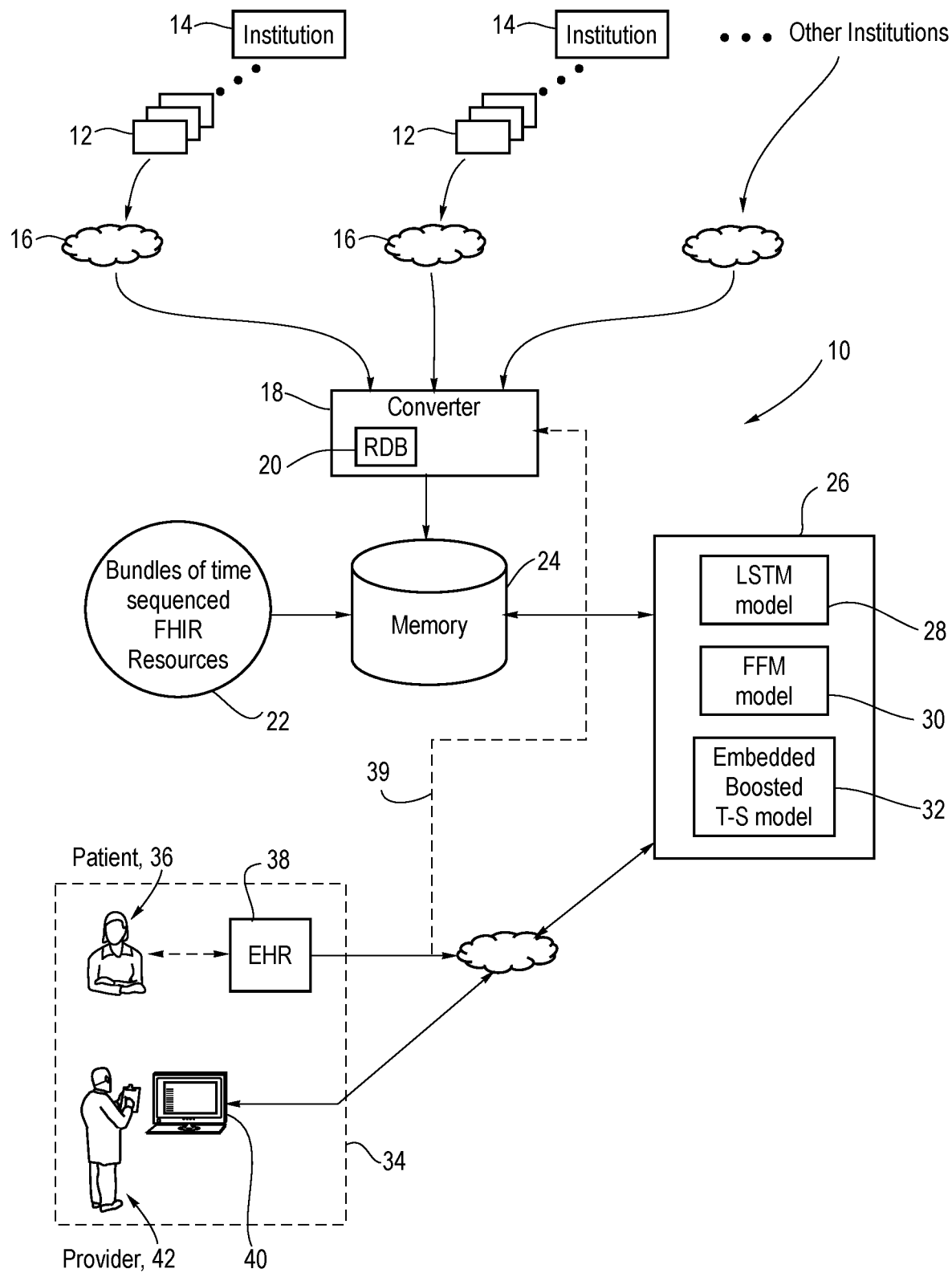
FIG. 1 is a schematic diagram of the overall system including aggregated electronic health records, computer executing trained deep learning models, and electronic device used by a healthcare provider which receives predictions and pertinent relevant past medical events related to the prediction from the deep learning models and has an interface to present such information on its display.

FIG. 1 illustrates a system 10 for predicting and summarizing medical events from electronic health records. The system includes three components:

First, there is described a computer memory 24, e.g. mass data storage device, storing aggregated electronic health records 22 from a multitude of patients of diverse age, health conditions, and demographics including medications, laboratory values, diagnoses, vital signs, and medical notes (e.g. free text notes written by attending physicians and nurses). The aggregated electronic health records are converted into a single standardized data structure format and ordered per patient, e.g., into a chronological order. The raw electronic health records 12 of large numbers of patients from different institutions 14 (e.g., university medical centers, hospital systems, etc.) may be formatted in various different electronic formats due to the wide variety of legacy electronic health records systems currently in use. The raw health records are patient de-identified and are transmitted over computer networks 16 and stored in a relational database (RDB) 20 and converted by a computer system 18 functioning as a converter into a standardized format and stored in the memory 24. These records are converted into the standardized data structure format and arranged in an ordered arrangement, in a preferred embodiment in time sequence. In one particular embodiment, the standardized data structure format is the Fast Health Interoperability Resources (FHIR) format, a known format, in which the EHRs are formatted in bundles of time-sequenced FHIR "resources" shown as 22 in FIG. 1. This will be described later in conjunction with FIG. 2.

Secondly, the system includes a computer 26 (the term is intended to refer to a single computer or a system of computers or processing units sharing a processing task, together with ancillary memory) executing one or more deep learning models (28, 30, 32, described below) trained on the aggregated health records 22 converted into the single standardized data structure format and in the chronological order. The deep learning models are trained to predict one or more future clinical events and to summarize pertinent past medical events (e.g., problems, conditions, test results, medications, etc.) related to the predicted one or more future clinical events on an input electronic health record 38 of a given patient 36. The input health record 38 is in the standardized data structure format and ordered into a chronological order, as is the case with the aggregated health records used for model training. The input health record 38 could be converted if necessary to the FHIR format by the converter 18 as indicated by the dashed lines 39.

It will be appreciated while FIG. 1 shows the receipt of an input electronic health record 38 from a single patient, in practice this may be occurring essentially simultaneously for other many other patients across a medical system or hospital depending on the extent of the roll-out of the system.

The system of FIG. 1 preferably employs sufficient computing resources for the computer 26 (or system of computers) to operate the models on the input health records and generate data as to predictions and relevant past medical events to the predictions for all these patient EHRs simultaneously in real time and transmit the data to the electronic device(s) 40 for display on the client-facing interface of the device.

Thirdly, the system includes an electronic device 40 for use by a healthcare provider treating the patient, e.g., computer terminal or workstation, tablet, smartphone or other type of computing device having a screen display, which is configured with a client (healthcare provider)-facing interface (FIGS. 8A-8B, 9, 14, etc.) displaying the predicted one or more future clinical events and the pertinent past medical events of the patient. The display of the future predicted clinical events and relevant past medical events assist the healthcare provider 42 (for example, nurse or doctor) to focus their attention on highly relevant information in the patient's electronic health record that is pertinent to predictions, such as prediction of ICU transfer, late discharge, mortality, etc. Examples of the usage of the device 40 and interface to provide this assistance is described later in conjunction with FIGS. 8A-19 and in the Examples.

In another aspect of the disclosure, a method is described for predicting and summarizing medical events from electronic health records. The method includes the steps of:

a) aggregating electronic health records 12 from a multitude of patients of diverse age, health conditions, and demographics, the electronic health records including medications, laboratory values, diagnoses, vital signs, and medical notes;

b) converting the aggregated electronic health records into a single standardized data structure format and ordered per patient into an ordered arrangement (see bundles of time-sequenced FHIR resources 22 generated by the converter 18);

c) training one or more deep learning models 28, 30 and 32 on the aggregated health records 22 converted into the single standardized data structure format and in the ordered arrangement;

d) using the trained one or more deep learning models 28, 30 and 32 to predict one or more future clinical events and summarize pertinent past medical events related to the predicted one or more future clinical events from an input electronic health record 38 of a patient 36 having the standardized data structure format and ordered into a chronological order; and e) generating data for a healthcare provider-facing interface (FIGS. 8A-8B, 14, 19, etc.) of an electronic device 40 for use by a healthcare provider 42 treating patient, the data displaying the predicted one or more future clinical events and the pertinent past medical events of the patient.

The component aspects of the system and method will now be described with greater detail.

Figure 2:
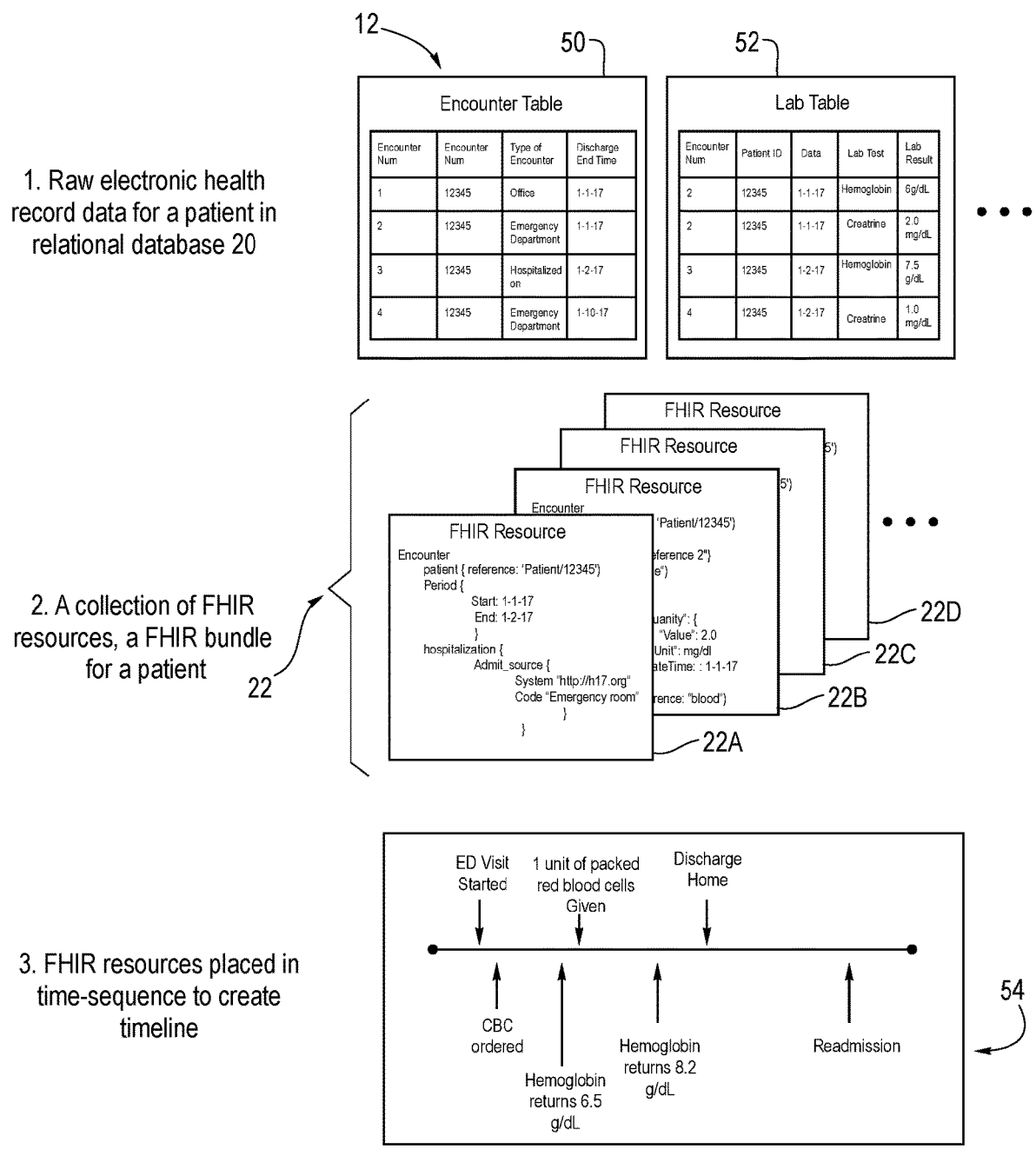
FIG. 2 is an illustration of the procedure used in the system of FIG. 1 for converting raw electronic health records into FHIR resources in time-sequence order.

B. Consolidation of Electronic Health Records into a Single Format for Model Generation As noted above, the raw electronic health records 12 may take the form of health records from a multitude of patients (hundreds of thousands or even millions of patients). The aggregated health records could be obtained from one or more different institutions. The EHR data may be in different data formats, due to lack of standardization in the industry. These records are converted into the standardized format and arranged in an ordered arrangement. This is shown at FIG. 2, in which the raw electronic health records 12 for a patient include encounter tables 50 (all visits of the patient to doctor offices, laboratories, hospitals, etc.), lab tables 52 containing all lab testing and results, as well as other tables (not shown) containing data such as vital sign data, medical notes (free text), demographic data, diagnoses, flow sheets, etc. The patient data is anonymized; no personal identification data is included. Permission to receive the data and use it to train the models is obtained from the institutions. These tables 50, 52 representing the raw data are stored in the RDB 20 of FIG. 1. The converter 18 then converts the raw data into a standardized format, in this example a collection of FHIR resources 22A, 22B, 22C, 22D, etc. as shown in FIG. 2, and for each patient there is a "bundle" or set 22 of such FHIR resources. As indicated at 54 in FIG. 2, these resources are then placed in time sequence order to create a timeline or chronological order of all the data in the EHR.

Details of the data sets we used to generate our predictive models are set forth in Appendix A of our prior U.S. provisional application Ser. No. 62/538,112 filed Jul. 28, 2017. Briefly, in our model development, we obtained electronic health record data from the University of California, San Francisco (UCSF) in San Francisco, Calif., University of Chicago Medicine (UCM) in Chicago, Ill., and Beth Israel Deaconess Medical Center in Boston (MIMIC-III), Massachusetts. These electronic health records were in de-identified or limited data set form shared in compliance with all state and federal privacy laws (including HIPAA). We also used a de-identified national database of Medicare and commercial claims, known internally as "Uranus," with records of 2 billion encounters across 70 million patients, between 2013 and 2015. The UCSF data contains all patients with encounters between 2011 and 2016 from an academic medical system with several hospitals of varying sizes. UCM de-identified data contains all adult patient encounters between 2009 and 2016 from several hospitals. The MIMIC de-identified dataset contains data associated with patient encounters in critical care units in in Boston, Mass. from 2001 and 2012. Of course, electronic health records could be aggregated and obtained from other institutions, so the specifics of the development set are not believed to be particularly important but a sufficiently large set should be used in order to improve accuracy of the models.

Each EHR dataset contained patient demographics, all inpatient and outpatient encounters, orders entered in the EHR, diagnoses, procedures, medications, laboratory values, vital signs, and flowsheet data, which represents all other structured data elements (e.g. nursing flowsheets). In addition, the datasets from UCM and MIMIC-III contained de-identified medical notes, and the dataset from UCM also contained intraoperative vital sign and outpatient surgical flowsheet data.

The Uranus claims dataset included patient demographics, all inpatient and outpatient encounters, diagnoses codes, procedure codes and outpatient medication prescriptions.

Data were de-identified except for the dates in the UCM dataset, which complied with all requirements for disclosure and use of a limited data set under HIPAA. Ethics review and institutional review board exemption was obtained from each institution. Patient data was not linked to any Google user data. Furthermore, for the aggregated electronic health records used to create the models our system includes a sandboxing infrastructure that keeps each EHR dataset separated from each other, in accordance with regulation, data license and/or data use agreements. The data in each sandbox is encrypted; all data access is controlled on an individual level, logged, and audited.

We developed a single data-structure for the aggregated EHRs based on Fast Healthcare Interoperability Resources (FHIR) to store data from each system that was used for all health systems and predictions. FHIR is an open-source framework that allows standardized representation of clinical data as a set of resources—modular entries that contain a specific data-type, like a single encounter or lab test. The various types of data collected by the health systems were converted into their corresponding FHIR resources.

When converting data to a FHIR format ("resources," see FIG. 2), we did not harmonize variable names to a standard terminology but instead used the raw terminology provided by the health system, bypassing the traditional time-consuming harmonization of data. The only exception was made for variables that were required to define primary outcomes and exclusion criteria: discharge disposition, hospital service, diagnosis codes and procedure codes. Hospitalization diagnoses were provided as ICD-9/10 codes, we mapped these to single-level Clinical Classifications Software categories (CCS; Agency for Healthcare Research and Quality); hospitalization procedures were provided as ICD-9/10 and Current Procedural Terminology (CPT) procedure codes and were also mapped to CCS codes.

Next, the set of resources for a given patient were assembled in chronological order. This sequence of events provided a faithful representation of the timeline of each patient in the EHR. Billing codes are assigned a timestamp immediately after the end of an encounter.

Certain elements, like vital signs, can be entered into the EHR after they were collected. We used timestamps for nursing documentation and vital signs corresponding to the entry of the data into the EHR rather than when it was recorded as collected to model the data as it would become available in an EHR in real time.

C. Deep Learning Models for Predicting Health Events from Medical Records

As shown in FIG. 1, our system includes a computer 28 (or equivalently set of computers or processors and ancillary memory) executing deep learning models 28, 30 and 32 trained on the aggregated health records 22 converted into the single standardized data structure format and in the chronological order. The models predict one or more future clinical events and summarize pertinent past medical events related to the predicted one or more future clinical events on an input electronic health record 38 of a patient 36. The input EHR is formatted in the same standardized data structure format and ordered into a chronological order, either natively or after conversion by the converter 18 if necessary.

While in theory one could just use a single trained model, in order to avoid overfitting and provide high accuracy in predicting future clinical events we have found it advantageous to use three different models, each of which are trained on data sets making up the aggregated electronic health records separately. At least one of the deep learning models contains attention mechanisms indicating how much attention (or equivalently, how significant) the model gave to "tokens" (i.e., atomic elements in the electronic health record such as individual words in a note, medications, lab results, etc.) to predict the one or more future clinical events and the related pertinent past medical events related to the predicted one or more future clinical events. The use of attention mechanisms in deep learning neural networks is described in the conference presentation of D. Bahdanau et al., *Neural Machine Translation by Jointly Learning to Align and Translate*, January 2014 (arXiv:1409.0473[cs.CL]. Further explanations of attention mechanisms in the context of healthcare include Choi et al., *GRAM: Graph-based attention model for Healthcare Representation Learning*, arXiv: 1611.07012v3 [cs.LG] April 2017 and Choi et al., *RETAIN: an Interpretable Predictive Model for Healthcare using Reverse Time Attention Mechanism*, arXiv:1608.05745v3 [cs.GL] February 2017. The content of the Choi et al. and Bandanau reference is incorporated by reference herein.

In our preferred embodiment, we use three different models: a Long-Short-Term Memory (LSTM) model 28, which is a weighted recurrent neural network model, a time aware Feed-Forward Model (FFM) 30 (also referred to herein as a Feedforward Model with Time-Aware Attention), and an embedded boosted time-series model 32, also referred to herein as a Feed-Forward Model with boosted, time-aware stumps. The Appendix B of our prior U.S. '112 provisional application and the description of FIG. 3A-3C gives further details on the architecture, design and implementation of the three models.

There are a variety of prediction tasks that can be performed by these models; several of which are described in some detail here and in Appendix A of our prior U.S. '112 provisional application. These include prolonged length-of-stay, unplanned hospital readmissions, unplanned transfer to ICU, inpatient mortality, primary diagnosis code and a complete set of billing diagnoses codes at discharge. These predictions are made without selection or engineering of predictor variables per task.

The outcomes of five prediction tasks are defined below. For every prediction we use all information available in the EHR (except for the claims database) up to the time at which the prediction is made: at hospital admission, after 24 hours or discharge. We selected 24 hours because this is commonly used in clinical prediction models such as APACHE. E.g., Zimmerman et al. *Acute Physiology and Chronic Health Evaluation (APACHE) IV: hospital mortality assessment for today's critically ill patients*, Crit. Care Med., 2006.

Admission time was defined as the start of an inpatient status, meaning data from the emergency department and outpatient surgeries would be available prior to admission.

For the MIMIC dataset, the time points were relative to ICU admission. As the claims data had only day-level attribution, predictions made on the day of admission included claims filed on the same calendar date as admission.

Inpatient Mortality

We predicted inpatient death, defined as a discharge disposition of "expired."

Long Length of Stay

We predicted a length-of-stay greater than 7 days, which was picked as approximately the 75th percentile hospital stays for most services across the datasets. The length-of-stay was defined as the time between hospital admission and discharge.

30-Day Unplanned Readmission

We predicted a future unplanned readmission within the subsequent 30 days after a discharge from a hospitalization, given all of the data elements above during and prior to the admission. There is no accepted definition of "unplanned" so we used a modified form of the Centers for Medicare and Medicaid Services (CMS) definition: readmissions were excluded if they were for planned procedures without acute complications, chemotherapy, transplants, or admission for rehabilitation, with details in the Appendix B of our prior U.S. '112 provisional application. A readmission was counted if the admission time was within thirty days of the prior discharge time of an eligible index hospitalization without any intervening hospitalizations (i.e. a readmission could only be counted once Diagnoses—Primary and Complete Set For each hospitalization we classified what the patient was most likely being treated for by predicting the primary diagnosis (using CCS categories, which cluster related diagnoses and procedures to approximately 250 groups such as septicemia or tuberculosis). We also predicted the entire set of primary and secondary ICD-9 billing diagnoses (i.e. from a universe of 14,025 codes). We used CCS categories for primary diagnosis to mimic an assignment that could be used for decision support, which would not require the exact ICD-9 code.

Inclusion and Exclusion Criteria in the Study Cohort

We included all consecutive admissions for patients 18 years or older, except for one data set where we used no age restriction to be comparable with literature. We only included hospitalizations of 24 hours or longer to ensure that predictions at various time points had identical cohorts.

To imitate the practical accuracy of a real-time prediction system we did not exclude patients typically removed by studies of readmission, like being discharged against medical advice, since these exclusion criteria are not known when predicting earlier in the hospitalization.

For predicting the full set of ICD-9 diagnoses, we excluded encounters without any ICD-9 diagnosis, which was approximately 2 to 12 percent per dataset. These were generally encounters after October, 2015 when hospitals switched to ICD-10. We included such hospitalizations, however, for all other predictions.

To compare with existing literature, we also created a restricted set of index hospitalizations to a medical or surgical services (i.e. excluding obstetrics).

Model Design and Training

We used three types of deep learning architectures for the models 28, 30 and 32 (FIG. 1) that accommodate modeling a sequence of patient events in an EHR. We used a well-known version of a recurrent neural network named the Long-Short-Term Memory (LSTM) (see Hochreiter S, Schmidhuber J., *Long Short-Term Memory*. Neural Comput. 9 pp. 1735-1780 (1997), the content of which is incorporated by reference herein, to create model 28. We created two new methods that we call a time-aware feedforward model (FFM) to create model 30 and an embedded boosted time-series to create model 32, which we describe in the Appendix B of our prior U.S. '112 provisional application. For the first two models 28 and 30 we implemented attention mechanisms (see the Bandanau et al. paper cited previously) to highlight the data elements that most affected the prediction. Each model was geared towards addressing specific challenges with EHR data: long sequences of patient events, dynamic changes in variables, and the effect of remote historical patient data.

Each model 28, 30 and 32 was trained on each dataset in the cohort separately. For predictions, in most some instances we took the average of the predictions from each model to come up with the final prediction score. In other instances we exclude results from one of the models, e.g., where it is not tuned for a particular task or prediction and average the prediction scores of the remaining models.

Patient EHRs were randomly split into a development set (80%), a validation set (10%) and a test set (10%). To prevent any implicit overfitting, the test set remained unused (and hidden) until final evaluation. Model accuracy is reported on the test set and bootstrapping of the test set 999 times was used to calculate 95% confidence intervals. As the goal was to create personalized predictions and not evaluate contributions of individual predictors, we ignored within-patient clustering.

For each prediction task, we created baseline models with hand-crafted variables based on existing literature in order to judge retrospective model performance. Details about the baseline models are described in Appendix B of our prior U.S. '112 provisional application. The LSTM and FeedForward models 28 and 30 were trained with Tensorflow (Version 1.0) and the boosting model 32 was implemented with custom C++ code. Statistical analyses and baseline models were done in SciKit learn Python (0.18.1).

All models learn embedding vectors to represent each token (e.g., atomic element of an EHR). A token, for example, could be a word in a note, the name of a medication, or a discretized value of a particular lab test. The embeddings were randomly initialized, and the model training updated the embeddings to improve predictive performance.

FIG. 3A is a flow chart illustrating the design and implementation of the FFM 30 of FIG. 1. The steps are essentially as follows Step (1) shows the data in the original EHR, with relative timestamps (delta time) to e.g., the moment of prediction.

Step (2) shows that each data element is embedded, which means converted to a d-dimensional vector (this conversion is learned by the model).

Step (3) shows that each delta time is embedded, which means converted to a k-dimensional vector using k functions which together encode a piecewise-linear split (this conversion is learned by the model, resulting in a bank of pre-defined or learned functions $A_1 \ldots A_k$).

Step (4) shows that a learned projection matrix is multiplied by the data embedding to result in an attention data projection matrix, which is multiplied by a time embedding matrix using column dot product operator, resulting in alpha ($\alpha$) vector.

Step (5) shows that a vector is put into a softmax function, resulting in a beta ($\beta$) vector.

In step (6) beta vector is multiplied by the data embedding matrix, resulting in a reduced record vector of dimension D which is entered into a feedforward network (i.e., several layers of an internal ReLu (Rectified Linear Unit)) with a sigmoid or softmax function at the end, resulting in a prediction output.

The output of the model is the output of the sigmoid, plus the learned attention vector from step (4).

FIG. 3B is a flow chart showing the design and operation of the embedded boosted time series model 32 of FIG. 1. The steps are essentially as follows: step (1) shows the data in the original EHR, with relative timestamps (delta time) to e.g., the moment of prediction. In step 2) each data element is turned into a binary feature $f_0 \ldots f_N$ indicating existence of a particular value/token at a particular (relative) point in time. Each predicate of the form v>V at some t>T. Together these form a N-bit vector V.

In step (3) vector V is multiplied with a (learned) embedding vector E of dimension D, and aggregated (e.g., summed), resulting in a D-dimensional vector.

In step (4) this D-dimensional vector is entered into a network of e.g., several ELU (exponential linear unit) layers, ending with a sigmoid. The output of the network is the output of the sigmoid function.

FIG. 3C is a flow chart showing the design and operation of the LSTM model 28 of FIG. 1. The steps are essentially as follows:

(1) For each feature category (e.g., medications, notes, vital signs), each data point is embedded in a $D_{category}$-size vector.
(2) All data is considered in bags of e.g., 1 day. Per feature type, a weighted average is calculated for all vectors in the bag, yielding e.g., the average medication vector for that bag.
(3) Per bag, e.g., one day, all average feature vectors are concatenated, yielding a vector of size $D=D_{medication}+D_{note}+D_{vital}$, etc., for all feature types.
(4) Those average vectors are entered into an LSTM model, with each vector representing one step in the sequence.
(5) The output of the LSTM is entered into either a softmax function (for multiclass classifications, e.g., identifying the primary diagnosis) or a logistic function (for probability tasks, e.g., mortality).

Alternatives to these models may be suitable for use in the present system, such as, for example autoregressive convolutional neural network models with attention, see A. Vaswani et al., Attention is all you need, arXiv:1706.03762 [cs.CL] (June 2017).

As noted above, the models use attention mechanisms which enable a granular visualization of the weights or "attention" to particular tokens used by the models to make a particular prediction for a patient. Several examples will now be described in conjunction with FIGS. 4, 5 and 6.

Figure 4:
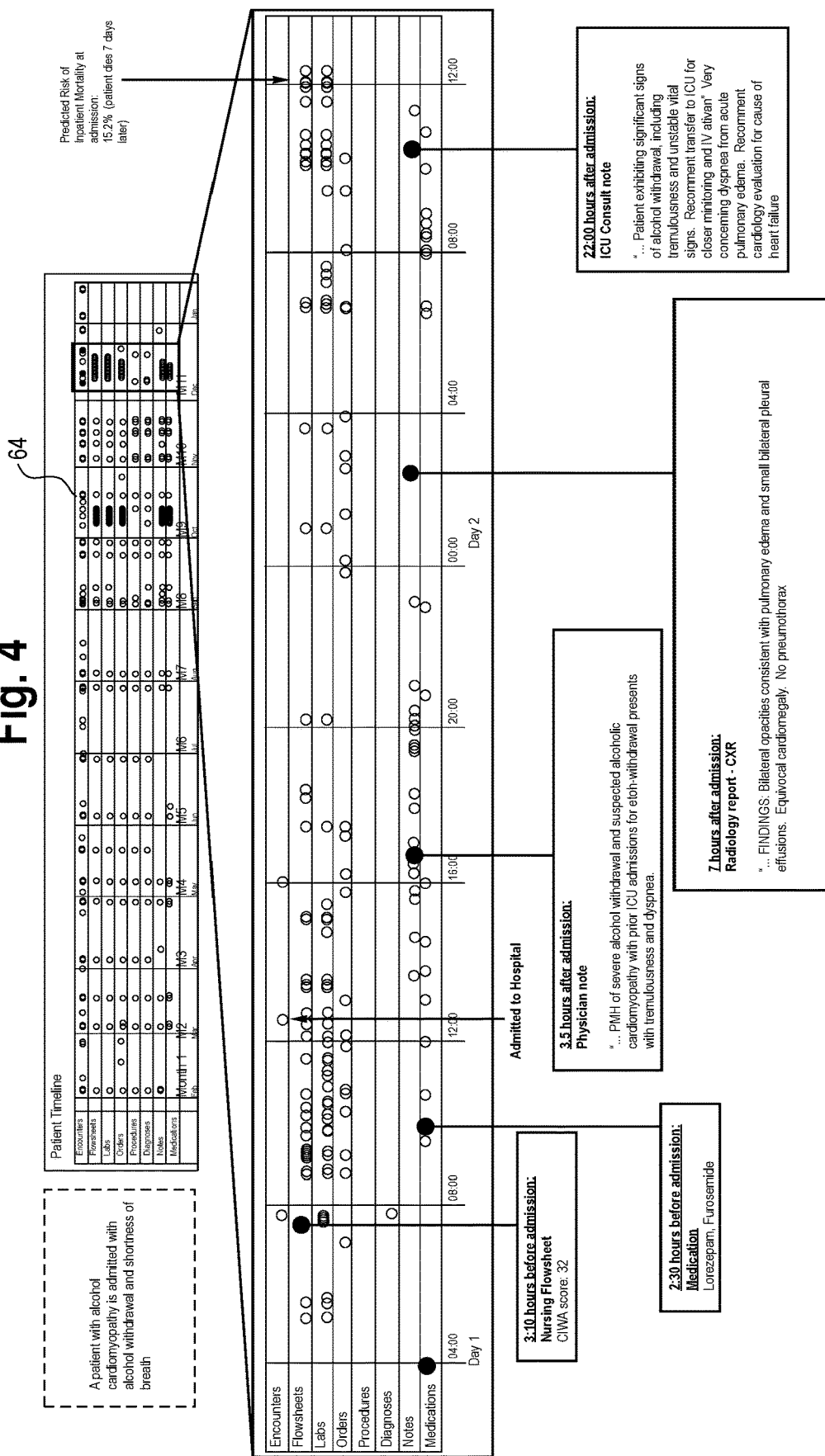
FIG. 4 is an illustration of one form of display of data on a provider-facing interface showing results of an attention mechanism in the deep learning models in a patient timeline or series of events including medications, encounters, procedures, notes, orders, etc.

FIG. 4 is an illustration of one form of display 64 of data in an EHR showing results of attention mechanism in the deep learning models in a patient timeline or series of events including medications, encounters, procedures, notes, orders, etc. In this particular example each circle indicates occurrence of a particular event related to a prediction (in this case predicted risk of inpatient mortality), such as administration of a medicine, a lab test, procedure, note or order. The timeline indicates the date patient was admitted, and excerpts of their record (e.g., medications, notes, reports, etc.) at particular points in time over two days in this example. FIG. 5 is an illustration of another form of display of data in an EHR showing results of attention mechanism in the deep learning models in the form of excerpts of notes with degrees of emphasis (size, boldness, etc.) given to individual words in the notes corresponding to the attention (significance, or weight) the words were to a clinical prediction generated by the deep learning models, and particular medications in the medical history were to the prediction (diagnosis of metastatic melanoma with pneumonia and anemia). The terms "melanoma", "metastatic", "encasement", "hemoptysis" etc., from free text notes in the EHR are shown in larger font and darker color to direct the attention of the provider that these elements of the EHR are pertinent or related to a prediction generated by the model. FIG. 6 is another example of results of the attention mechanism in the deep learning models, showing different words found in the notes of the EHR being afforded different degrees of emphasis (boldness, font size) being relevant to a prediction of a diagnosis of alcohol-related disorder. The darker highlights correspond to words in medical notes higher attention scores: abuse, withdrawal, drinker, etc. Further examples of attention mechanisms in the models to drive display of medical events in an EHR pertinent to a prediction will be discussed in a later section on the provider-facing interface.

An example of how the attention results of FIGS. 4, 5, and 6 are generated is as follows: First, to identify the past medical problems of the patient related to a prediction, we run the model that identifies diagnosis codes (as explained previously, ICD9 code prediction and primary diagnosis CCS code prediction) over all historical time periods of the patient (say, once per historical encounter, or once for each week in the history). From that we get a list of predicted/identified past medical problems, that we thus inferred from medications, labs, vitals, notes etc.

These problems are ranked and presented to the physician. The ranking depends on several factors such as (1) how much evidence supports this medical problem (e.g. is it only mentioned in the note, or also observed in the labs/vitals, and also treated with medications), (2) has this problem been explicitly billed for and coded in the main EHR, or is this an "embedded" diagnosis that we inferred but was not explicitly coded or billed for, and (3) how rare and severe is this medical problem (e.g. aneurysm vs hypertension), and potentially other factors.

Next, for each problem, we need to summarize key facts such as key medications and key note excerpts and words. We interrogate the above model (which classified this patient as e.g. having hypertension), using an attention mechanism, to indicate, e.g. for each medication or for each word in the notes, a number between 0-1 of how much attention (or, intuitively, weight or significance) the model gave to that word. The highest scored words are shown in these illustrations of FIGS. 5 and 6.

As another example, as will be described in later figures, the provider-facing interface of the electronic device (FIG. 1, 40) shows note excerpts from the EHR related to the prediction of ICU transfer (instead of a historical medical problem). Here we use again exactly the same attention mechanism to get a number between 0-1 for each input token seen by the model (e.g. for each word in the notes, for each medication prescribed etc.), indicating how much weight the model put on that individual word/medication/etc. while making the prediction of the ICU transfer.

Figure 7:
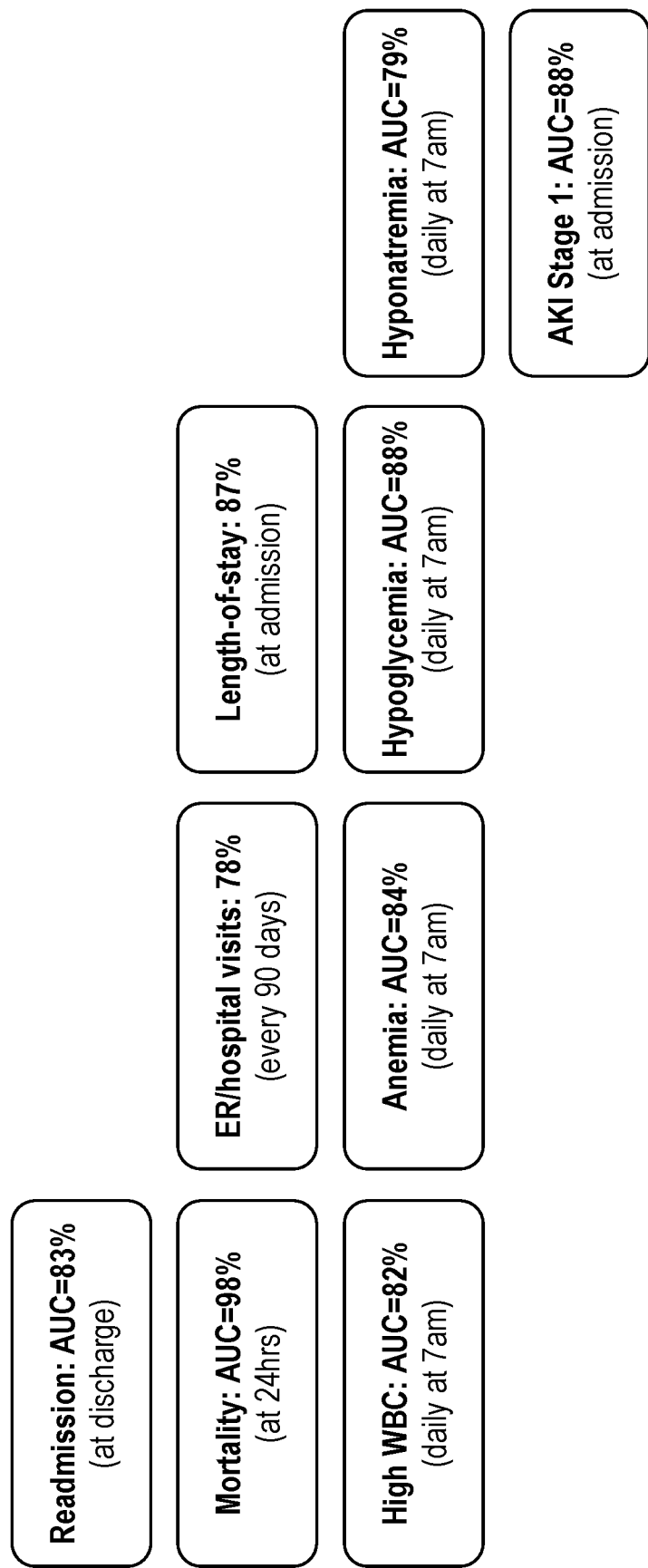
FIG. 7 is an illustration of different types of predictions which the models of this disclosure may be used to make, including atypical laboratory results, along with accuracy statistics obtained from applying the models retrospectively to a test set portion of the original set of patient records used for model training.

Further details on the model performance, the study cohorts, characteristics of the data sets, and results as compared to baseline models, are set forth in the Appendix A of our prior U.S. '112 provisional application and are not particularly pertinent. A summary of the results of performance of our models in a retrospective study of the test set in the cohort is shown in FIG. 7. FIG. 7 shows different types of predictions made by the models, including readmission, mortality, unplanned ER/hospital visits, etc. The "AUC" performance metric represents a receiver operating characteristic area under the curve, a standard performance metric in machine learning.

A summary of our findings from development and testing of the models is as follows. Using deep learning on electronic health record data, we have demonstrated highly predictive performance in predicting in-hospital mortality, long length-of-stay, unplanned 30-day readmission, identifying primary diagnoses, and assigning billing codes at discharge. We showed that results are consistent across healthcare systems and clinical tasks, improve with availability of new patient data, and interpretable with use of attention mechanisms. We have four key findings, described below. Further details are found in Appendix A of our prior U.S. '112 provisional application.

Results are Scalable Across Disparate Datasets

First, our method accommodates unstructured data such as free text notes across multiple clinical sites and can use all data in an EHR to for model training and create accurate predictions. Our approach does not require handpicking of variables and determining of how to clean, extract, and harmonize them from a particular site's raw data. Predictive models in the literature use a median of 27 variables, whereas we used a median of over 100,000 data-points, including variables that are typically difficult to include, like clinical notes and flowsheets.

Predictive Performance is Excellent Across Disparate Tasks

Second, our results suggest that our method of representing and modeling EHR data is scalable across clinical tasks, and we believe our results are superior to comparable studies for mortality (0.94-0.98 vs 0.91), readmission (0.74-0.75 vs 0.69) and length of stay (0.86-0.92 vs 0.77). Our performance on ICU mortality and hospital readmissions also outperforms discrimination by physicians.

Comparing our results to other studies, however, is difficult given that performance differs based on cohort selection and study design; many results have incomplete description of cohorts and outcomes, predict on smaller, disease-specific cohorts or use data not routinely available in real-time.

To address this limitation, we implemented versions of the HOSPITAL, NEWS score, and Liu's model as baselines, see Appendix B of our prior U.S. '112 provisional application, and demonstrate superior performance. We also evaluated a cohort designed to be more similar to those in related studies of patients on medical or surgical services and found similar benefit to our approach.

Additionally, we used an open-dataset, MIMIC, where we outperformed existing literature with AUC for mortality of 0.91 vs 0.80 and micro-F1 for ICD-classification of 0.4 vs 0.28.

Modeling Harnesses Value from the Full Sequence of Data

Third, our modeling techniques successfully update predictions as new data becomes available as opposed to using a fixed point in time. On all tasks, the models use hundreds of thousands of patient attributes to make substantial gains in performance on all tasks. Interestingly, our models extract discriminative performance from claims data nearly comparable to those on EHR data; indeed, on predicting unplanned readmissions, performance on claims exceeds performance on EHR data, likely due to a complete view on readmissions at other hospitals.

Output of Complex Models are Interpretable

Fourth, we demonstrate an attention mechanism that enables a granular visualization of data used by the model to make a particular prediction for a patient (see FIGS. 4-6 and the following discussion of the interface in FIGS. 8-9 and 14-19). Since we explicitly model the sequence and timing of patient events, our method indeed shows the what, when and where in a patient's history relevant to a prediction. Despite not having an analog to an odds ratio to describe how each variable contributes to the outcome, we believe attention techniques may alleviate concerns that deep learning is a "black box," and could, in the future, be used to extract salient information for clinicians. The presentation of underlying past medical events that are relevant to predicted future clinical events in the interface gives the healthcare provider confidence that the deep learning models in fact are providing information that is timely and useful.

Limitations

Labels in the dataset used for model development and training may be clinically incorrect or missing. Billing diagnoses may not reflect clinical diagnoses; for example, pneumonia is increasingly coded as sepsis for administrative reasons. Similarly, readmissions commonly occur in a separate health system, and those records are typically not shared with the discharging hospital system. In the absence of complete data sharing between health institutions or a dataset with research grade phenotypes, this limitation affects all data that is collected in live clinical care.

A second limitation is that our approach relies on large datasets, powerful computing infrastructure, and complex algorithms, which require sophisticated engineering to replicate. However, this approach is what allows a single modeling architecture to achieve excellent predictive performance across a range of prediction tasks, and is within the ability of those skilled in the art in view of the present disclosure and accompanying appendices.

Finally, there have been concerns that using many variables invariably leads to overfitting. We allay this concern by reporting results on a held-out test set of patients not used during training, which estimates real-world performance, and by showing the result holds for 3 separate datasets. Further, the design of the models may including techniques to avoid overfitting.

While several types of predictions have been described above, the models can be used for other prediction tasks, including: Medications and dosages, both for purpose of auto-completing and of alerting to unusual dosages or unexpected prescriptions (source of medical errors).

Next words, sentences or paragraphs in a physician note, e.g., discharge summary, for the purpose of auto-completing or suggesting templates or parts of documentation, for physicians to review, edit and submit (writing documentation is a major time burden).

Predicting a wide variety of life-threatening events such as intubation, ventilation, changes in acuity of care (e.g. ICU transfers), organ support, transplants etc., for the purpose of monitoring and alerting to such events.

Predicting physiological deterioration on e.g. a daily basis, or before ordering lab tests, or before e.g., administering glucose (for the purpose of preventing e.g. hyper/hypoglycemia).

Predicting total cost of care, for the purpose of risk stratifying high-cost patients.

Predicting admissions and census (how many patients will be admitted at each ward) for the purpose of capacity planning.

D. Provider Interface for Clinical Predictions and Understanding Through Deep Learning Once the predictive models 28, 30 and 32 have been developed, tested and validated as described above, they can then be used to make predictions on an input EHR from a patient as shown in FIG. 1 to improve patient care. In this section of the document we will describe how these predictions, along with identification of pertinent past medical events (test results, diagnoses, notes, medications, etc.) in the EHR can be presented to a healthcare provider. In essence, the computer 26 of FIG. 1 generates data from an input health record as to predictions and relevant past medical events using the model(s) 28, 30, and or 32 and provides that data to the electronic device 40 for rendering on the interface.

Figure 8B:
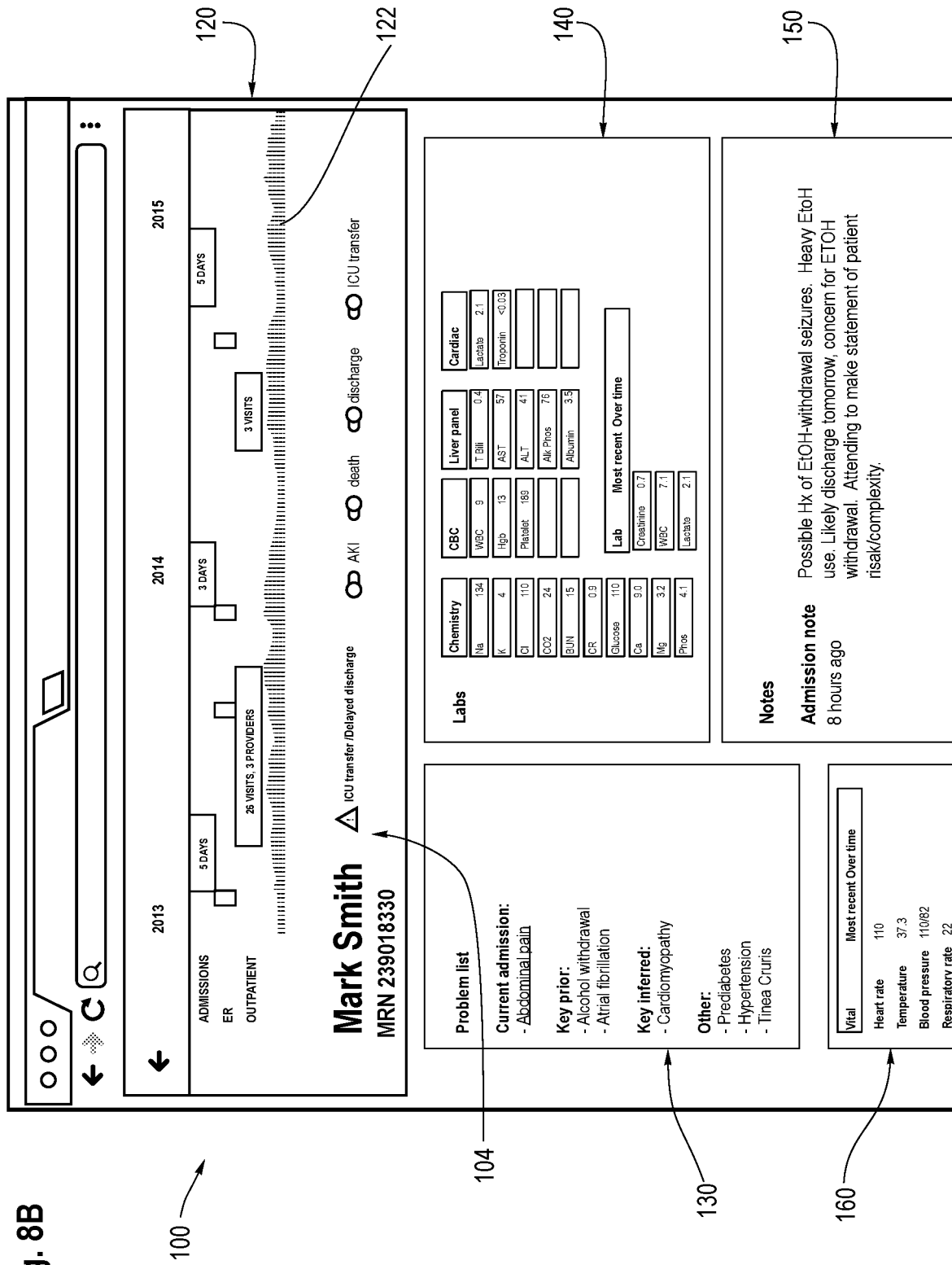
FIG. 8B is an illustration of the interface of FIG. 8A after the provider has selected the patient having the alert. The display helps the provider understand the patient now—by alerting them to key medical problems (medical events related to the prediction), dig into conditions or other data that he or she might need to look at to make a decision regarding patient care, including notes with results of attention mechanism of the models, and to not let them miss critical information.

FIG. 8A is an illustration of a healthcare provider-facing interface 100 of an electronic device 40 for use by a healthcare provider treating the patient, e.g., computer terminal, tablet, smartphone or other type of computing device having a screen display. The interface 100 in this configuration is designed for use in a hospital setting. The interface includes display areas 102 and 104 for two patients. For patient "Mark Smith", the display includes an alert 104 which indicates that the predictive models predict two future clinical events for this particular patient, in this case an unplanned transfer to intensive care unit (ICU) and a delayed discharge from the hospital. The interface of FIG. 8A is designed to alert the healthcare provider's attention early on to patients at risk. The system of FIG. 1 accurately predicts specific events where something is "off", "unusual", or "needing attention." From the physician's perspective, the interface meets the need to be alerted early, when they still have time to act. Furthermore, as will be explained in conjunction with FIG. 8B, the interface explains why the predictive models think/predict the alert condition will happen.

FIG. 8A also shows other aspects of interest, including a tool bar 108 which allows the physician to select a graphical display of different probabilities (or risks) in the timeline area 105 of the display 102, on a Y axis scale of 0-100. In this instance, the physician has toggled to the "on" position the risks/probabilities of death, discharge, and ICU transfer. Line 110 plots the probability of discharge from the hospital. Line 112 plots the probability of ICU transfer. Line 114 plots the risk of death. Note that approximately 16:00 there was a sharp spike in the in the risk of ICU transfer and shortly after that a slight increase in the risk of death. The physician can explore these plots of risks/probabilities and find out more information on past medical events related to the risk of ICU transfer and delayed discharge by clicking on or selecting the Alert icon 104.

When the Alert icon 104 is selected, the interface 100 changes to the display shown in FIG. 8B. Basically, this version of the interface helps the physician to understand the patient now, including the predictions that are made and relevant prior medical events. The physician is thinking: "What are the key medical problems I need to know about? Help me dig into the conditions or other data that I might need to look at to make a decision. Do not let me miss critical information." These needs are met by the display of FIG. 8B. In particular, in region 130 there is displayed of a problem list associated with the alerts: the chief complaint for the current admission (abdominal pain), key prior hospital admissions (alcohol withdrawal, atrial fibrillation), key inferred diagnosis (i.e., a diagnosis inferred by the models 28, 30, 32) based on the EHR in real time, and other key medical conditions of the patient (prediabetes, hypertension, and tinea cruris). In region 140 there is a display of current laboratory results. In region 150 there is a display of excerpts of medical notes which were pertinent to the predictions of ICU transfer and delayed discharge, with the results of the attention mechanism in the models highlighting in red font particular elements or words in the notes that were scored high by the attention mechanisms (in this case "EtOH-withdrawal", "concern for "ETOH withdrawal.") In region 160 there is a display of current vital signs. In region 120, there is a display of time lines showing prior hospital admissions, ER visits and outpatient activity. The line 122 is a visualization of the intensity of healthcare utilization of the patient, and the volume of data available about this patient, e.g., how often they have visited a healthcare facility, how many labs/vitals were taken, how many medications were prescribed etc.

Further discussion of the interface of FIGS. 8A and 8B will be provided below in the description of the Examples.

As noted previously, the predictive models can also be used in an outpatient setting in order to make predictions for a patient. For example FIG. 9 shows an interface 100 and the display of tools 200 on the interface that would be pertinent to use of the interface in a physician's office. The tools 200 allow the physician and his or her care team to plot timelines of risk/probability (similar to that shown in FIG. 8A, region 105) of emergency department visit, hospitalization, death and general cost/utilization of medical resources similar to the display line 202 of FIG. 8B.

Example 1—What Happens Today without the Benefit of this Disclosure

This hypothetical example will illustrate the difficulty in patient care without the benefit of the present disclosure.

Patient "Mark Smith" comes to the emergency room at 7 am for terrible abdominal pain. He has a full work-up, including labs and an abdominal ultrasound without a clear cause. His abdominal exam is relatively benign, but he still requires IV pain medications.

At 10 am, he is admitted to the internal medicine team for observation and pain control. The admitting team suspects non-specific gastritis, and they anticipate next-day discharge.

The primary team signs-out at 4 pm, handing over to a covering physician (responsible for 130 patients), and warning that: "Mr. Smith may develop alcohol withdrawal but there haven't been any signs yet." At 8 pm, the covering physician signs-out all 130 patients to the night doctor, Dr. Kingsley. At 8 pm, Dr. Kingsley enters for her overnight shift. She is covering 130 patients none of whom she has cared for previously. She starts her shift by forwarding the first-call pagers for all 130 patients to her own. At 10 pm, Dr. Kingsley receives a page.

Patient Smith in Room 14L-21, has heart rate 99, watching TV in bed comfortable. BP 115/79, RR 20, 98% RA. FYI as call parameter is 90

At 1:00 am, Dr. Kingsley gets another page.

Patient Smith in Room 14L-21 has sepsis alert, please call back at 3-9124

Dr. Kingsley logs into the EHR and sees an alert.

Sepsis alert. Patient meets SIRS criteria. Administer 30 cc/kg IV fluids and antibiotics within 1 hour, per national guidelines.

Digging deeper, Dr. Kingsley sees that the patient's heart rate has been creeping up from 70 in the daytime, to 99 and now 110, and his respiratory rate is recorded as 20 (the usual number recorded when the rate is normal). The lactate (ordered by the nurse) was 2.5 (mildly elevated). Dr. Kingsley's pager is now going off every 45 seconds, so she has to triage her time. At 1:05 am, she calls back the nurse who reports "he doesn't look great, he's a little shaky and diaphoretic." While she's talking, she's pulling up the note in the day where the primary problem is "unspecified abdominal pain." It continues "patient has non-specific abdominal pain and mildly elevated liver enzymes, ultrasound with non-specific gall bladder thickening. Suspect gastritis, maybe from alcohol use but patient denies. monitor for intra-abdominal pathology."

The sepsis alert reminded her of the clinical rule that for every hour antibiotics are delayed for sepsis, mortality goes up by 7.5%. She wants to see the patient but may not be able to examine him for another 30 minutes, which would make the delay of antibiotics likely more than 1 hour. She is worried about an intra-abdominal infection. She looks to see if he's ever had an echocardiogram, which he hasn't.

At 1:10 am, she orders 2L of IVF, vancomycin and zosyn (antibiotics), and orders a CT abdomen-pelvis with contrast.

2:10 am, an overhead alarm sounds.

CODE BLUE: 14L Room 21

Dr. Kingsley runs to 14-L Room 21 to find Mr. Smith in respiratory distress. The second bag of IV fluids is almost complete. She listens to his lungs and notices significant crackles that were not documented by the day team. His JVD is markedly elevated. She also notices his significant tremor and tongue-wag. The patient, when asked again, this time admits to drinking heavily in the past week but stopping 2 days ago because of the abdominal pain. She stops the IV fluids, calls the Intensive Care Unit (ICU) team to transfer the patient to the ICU for iatrogenic acute pulmonary edema and alcohol withdrawal.

The resolution of this example is as follows: The patient actually had gastric irritation from alcohol and ibuprofen use, causing his abdominal pain. While in the hospital, he started going into alcohol withdrawal, which was the cause of his elevated heart rate, tremor, and diaphoresis. The clinician also missed that his outpatient doctor was worried about alcohol cardiomyopathy because of worsening exercise tolerance and had ordered an echocardiogram that hadn't been done yet.

After being pulled into actually examining the patient from a code blue, the physician diagnosed acute pulmonary edema from the fluids she had ordered and recognized the alcohol withdrawal. The patient was transferred to the ICU, treated and discharged after 4 days. The patient was readmitted to the hospital 3 weeks later with C difficile colitis, likely from the incorrectly given antibiotics.

A root cause analysis asks what did Dr. Kingsley miss? The patient was evaluated hastily only after he had deteriorated. The patient had alcohol gastritis and withdrawal, which was mistaken for sepsis & mistreated. The patient had suspected cardiomyopathy: and should not have received fluids without physical exam and ECG. What should have happened?
1. Should have predicted and prevented pending ICU transfer for alcohol withdrawal.
2. Should not have given IV fluids, and thus prevented ICU transfer for fluid overload.
3. Should not have given antibiotics, and thus prevented the hospital-acquired infection.
4. Should have prevented the subsequent re-admission
Both a framing bias and confirmation bias help explain why this occurred. The framing bias is: do I withhold life-saving therapy for a patient with possible sepsis? The confirmation bias is that given the density of information, a physician looks only for source of possible abdominal sepsis.

Figure 13:
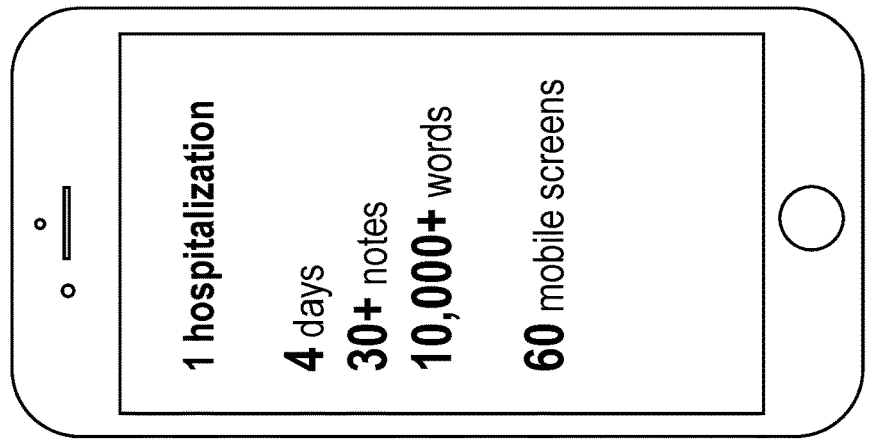

FIGS. 10-13 illustrate examples of the massive amount of information that is available to healthcare providers from EHRs and why the features of the present disclosure are needed. FIG. 10 shows excerpts from four years of this patient's medical history, with 433 listed diagnoses. FIG. 11 shows excerpts of diagnoses for this patent, but the lack of important accompanying information such as whether the patient was treated as an outpatient, inpatient, or in the ICU or other setting limits the usefulness of the information. FIG. 12 shows a huge list of different encounters for this particularly patient over a given time span, but lacks the detail on what happened in each encounter. FIG. 13 shows just one small fraction of the notes taken by providers in a single hospitalization over 4 days-33 notes totaling ~10,000 words, which would fill 60 different screens of a standard mobile device.

Simply put, there is a need to assist Dr. Kingsley in directing her attention to only those elements in the EHR that are actually relevant to the patient's current condition. Patient care in Example 1 can be improved, hence the development of the system of this disclosure.

Example 2—Predicted Clinical Event of ICU Transfer and Delayed Discharge

This example will illustrate the benefits of the system of FIG. 1 in the treatment of the patient "Mark Smith" in Example 1. In summary, the system alerts the physician's attention early to patients at risk, by accurately predicting specific events; alerts them early, when they still have time to act, and explain why the system is making the prediction. Once they have the attention (for example by the use of the alerts of FIG. 8A) it helps the physician understand the patient now—what are the key problems, what are the conditions and other data that the physician might need to look at to make a decision, and not let them miss critical information.

Figure 14:
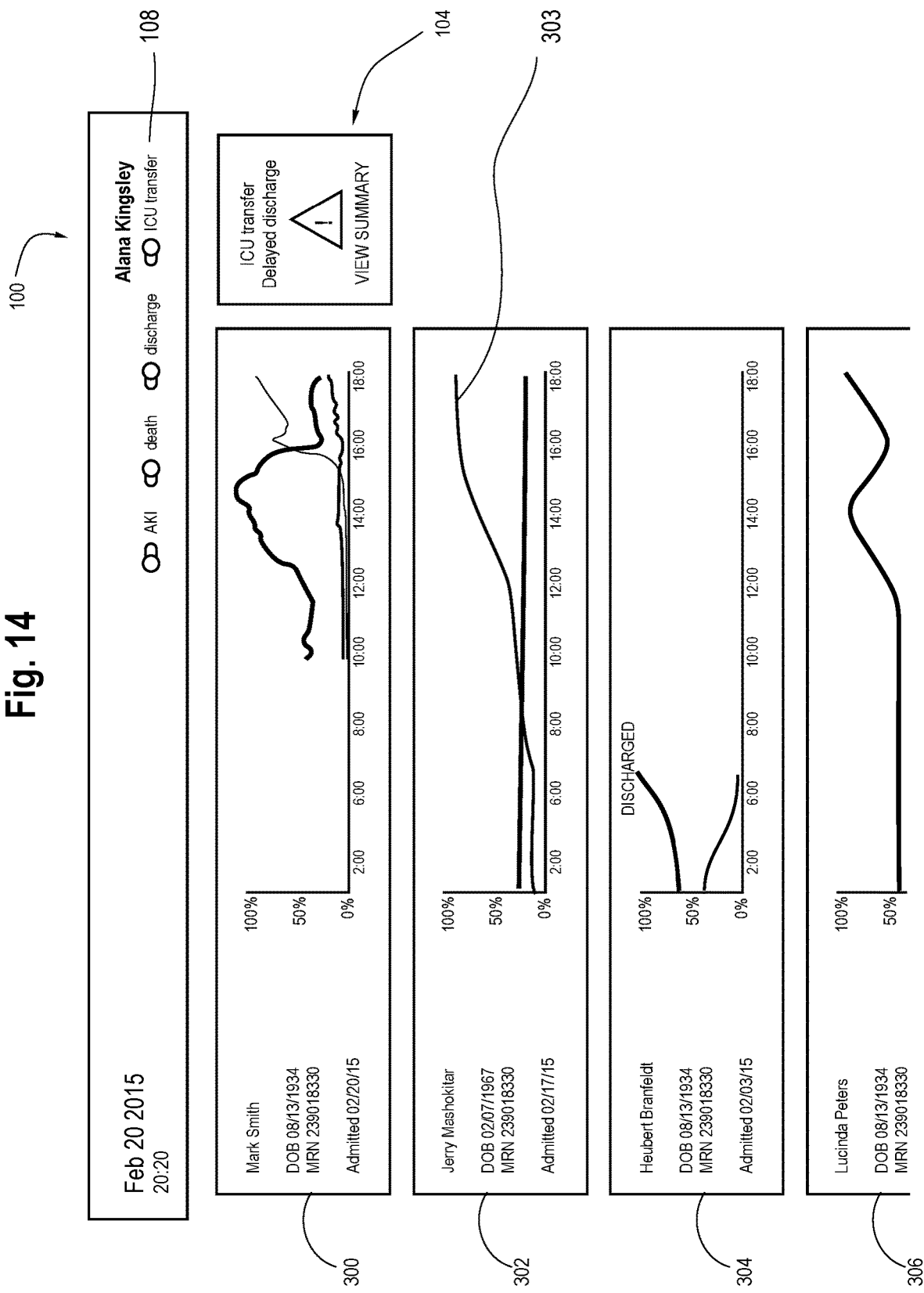
FIG. 14 shows an example of the interface of the device of FIG. 3 tracking data and risks for four patients in real time.

In FIG. 14 an example of the interface 100 of the device of FIG. 3 tracking data and risks for four patients in real time. The physician has toggled the tools 108 to customize the tracking of risks or probabilities in real time. In FIG. 14, the interface includes four display areas 300, 302, 304 and 306 for four different patients, the display area 300 is the display area for patient Mark Smith and the plots and alert 104 is as described in FIG. 8A.

In our hypothetical example, at 8:02 pm Dr. Kingsley starts her 8 pm shift and logs into the system providing the interface 100 of this disclosure, which is termed "Guardian" in this document. She first looks at Jerry Mashokitar who she was told was a "watcher", which is confirmed by Guardian, as the plot shows increasing risk of death indicated by line 303. At 8:03 pm, the alert 104 is activated she notices Mark Smith at the top of the patient list. The alert is that this patient is at risk of ICU transfer and delayed discharge.

Questions immediately form in Dr. Kingsley's mind: What are the patient's active medical problems? How severe was their alcohol withdrawal in the past? Did they require ICU stays? What treatments are they on for heart failure? Do they have a reduced ejection fraction? Have they had prior infections or received antibiotics recently? Any positive cultures? Has atrial fibrillation been hard to control? Did the patient suddenly stop taking beta-blockers? In other words, what are the key problems with the patient, when, and what is the evidence?

Dr. Kingsley activates the icon 104 and the display of FIG. 8B appears. The interface shows the risk of ICU transfer and draws her attention to the concern for alcohol withdrawal that drives that risk, by virtue of the notes region 150 showing excerpts of notes "Possible Hx of Et-OH-withdrawal seizures", "Heavy EtOH use" and "concern for ETOH withdrawal." The phrases "EtOH-withdrawal and "concern for ETOH withdrawal" are shown in red font and bolded. This is a result of the use of the attention mechanisms in the predictive models as explained previously. Thus, the display of FIG. 8B summarizes the past medical events for the predicted current risk (ICU transfer).

Figure 15:
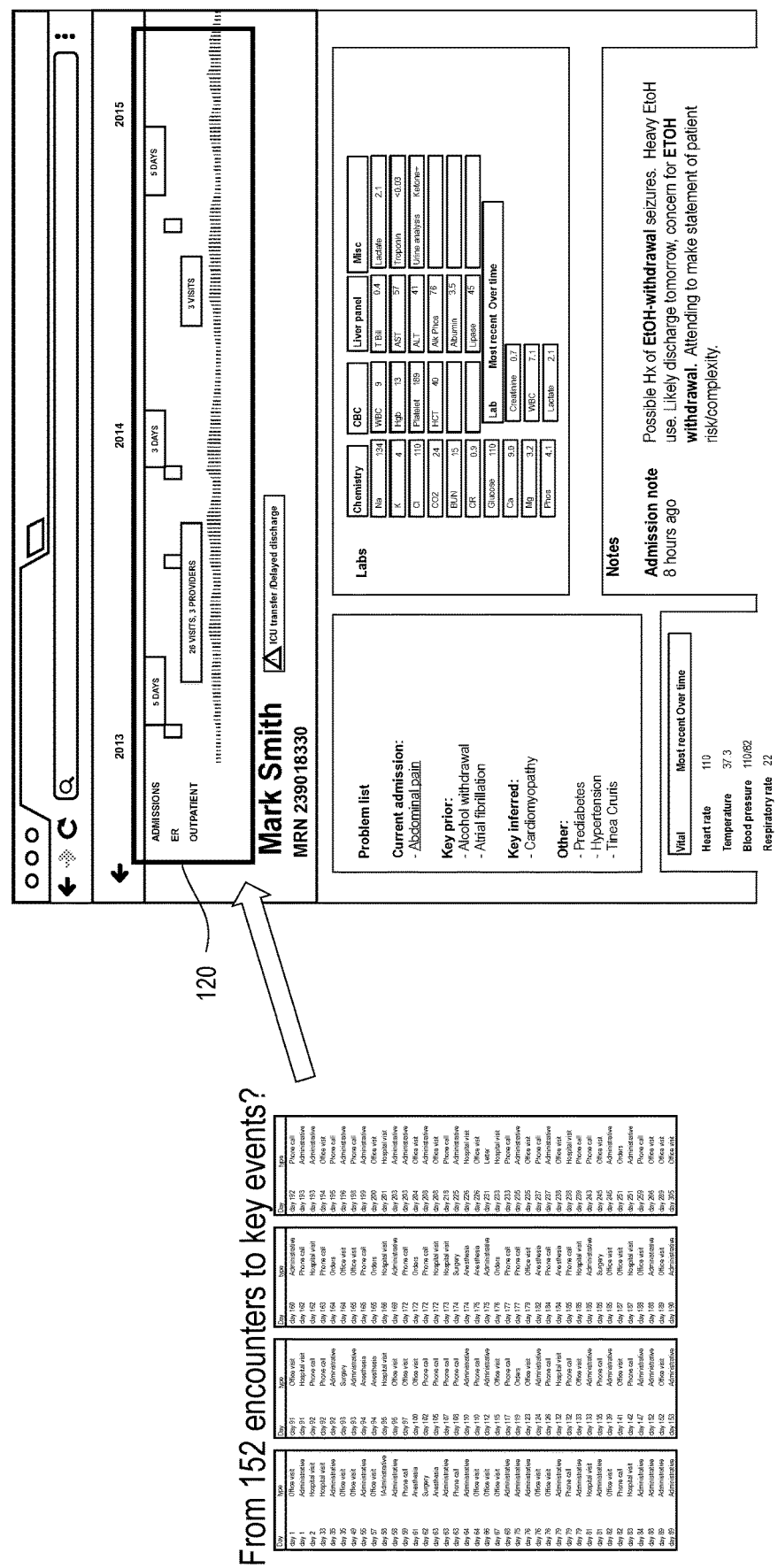
FIG. 15 shows the interface of FIG. 8B showing the selection of just the key events in the 150 past encounters in the EHR which are relevant to the predictions (ICU transfer, delayed discharge) and presented in a patient timeline.

FIG. 15 shows the interface of FIG. 8B showing the selection of just the key events in the 152 past encounters in the EHR which are relevant to the predictions (ICU transfer, delayed discharge) and presented in the patient timeline area.

Figure 16:
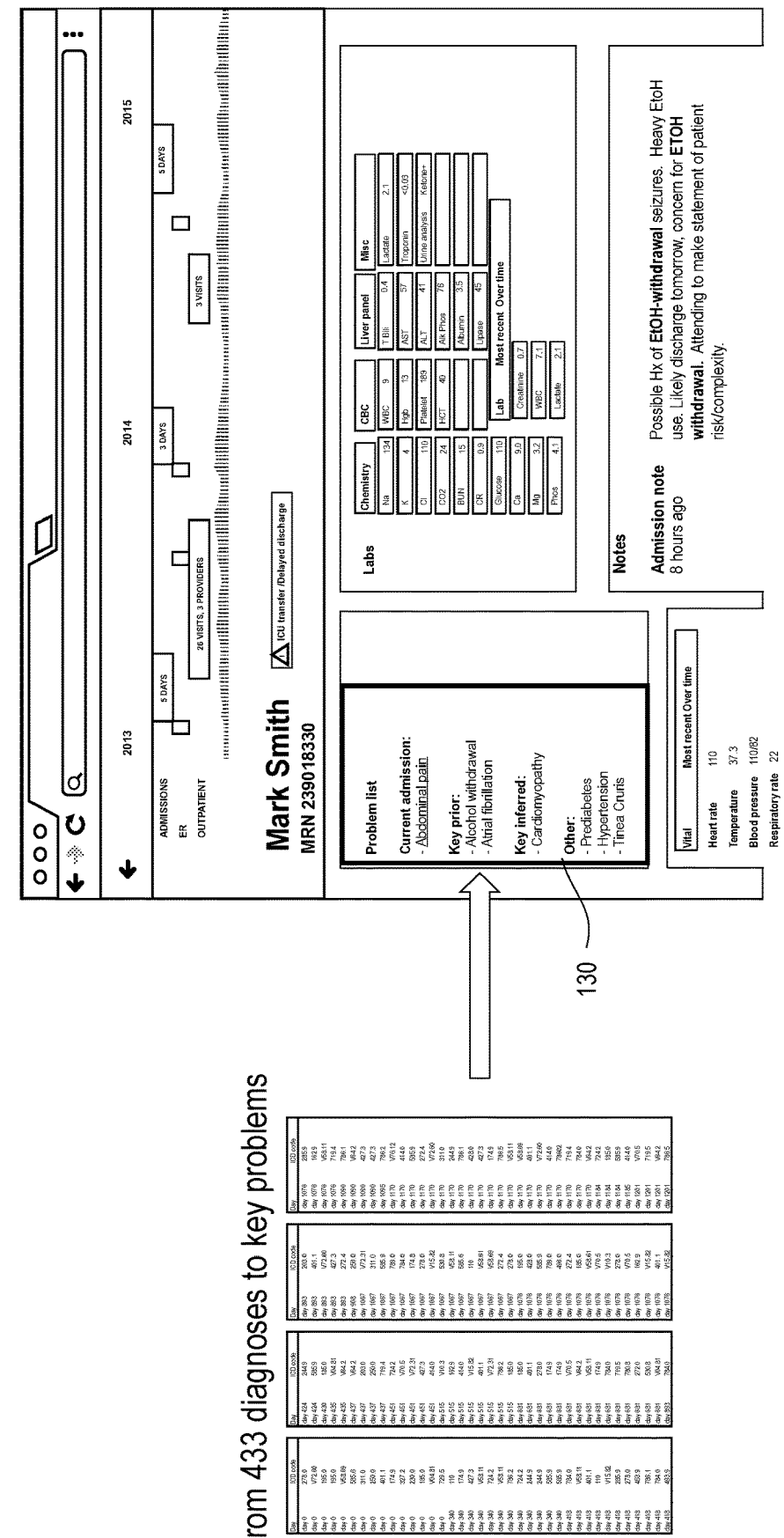
FIG. 16 shows the interface of FIG. 8B showing the selection of just the key problems from the list of 400 past diagnoses in the EHR which are relevant to the predictions (ICU transfer, delayed discharge). The key problems (i.e., pertinent past medical events) are presented as a summary in the left-hand side of the display in the problem list area.

FIG. 16 shows the interface of FIG. 8B showing the selection of just the key problems from the list of 433 past diagnoses or problems in the EHR which are relevant to the predictions (ICU transfer, delayed discharge). The key problems (i.e., pertinent past medical events) are presented as a summary in the left-hand side of the display in the problem list area.

Figure 17:
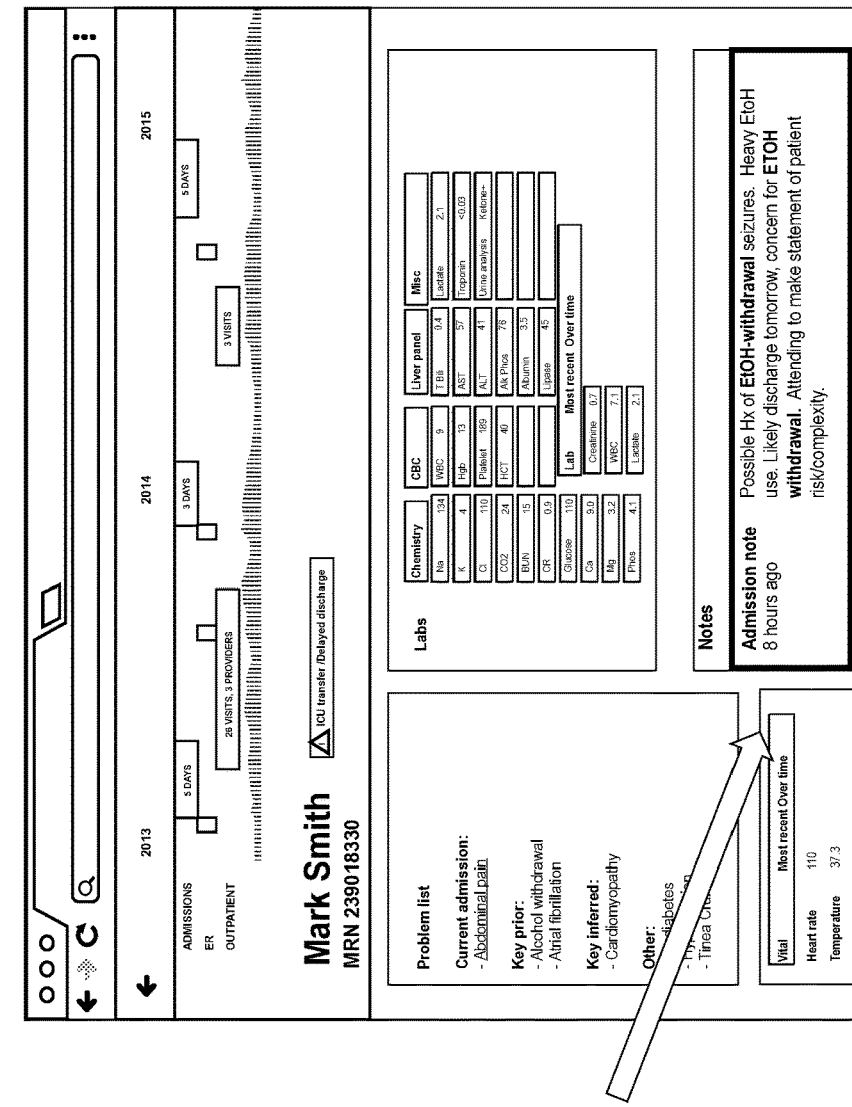
FIG. 17 shows the interface of FIG. 8B showing the selection of just the key, important excerpts or words from the 10,000 words in the notes in the EHR which are relevant to the predictions (ICU transfer, delayed discharge). The key excerpts (words and phrases) and presented in the lower right area of the interface, with degrees of highlighting to particular words or phrases as a result of the use of the attention mechanism in the deep learning models when generating the predictions.

FIG. 17 shows the interface of FIG. 8B showing the selection of just the key, important excerpts or words from the 12,000 words in the notes in the EHR which are relevant to the predictions (ICU transfer, delayed discharge). The key excerpts (words and phrases) and presented in the lower right area of the interface, with degrees of highlighting to particular words or phrases as a result of the use of the attention mechanism in the deep learning models when generating the predictions.

Figure 18:
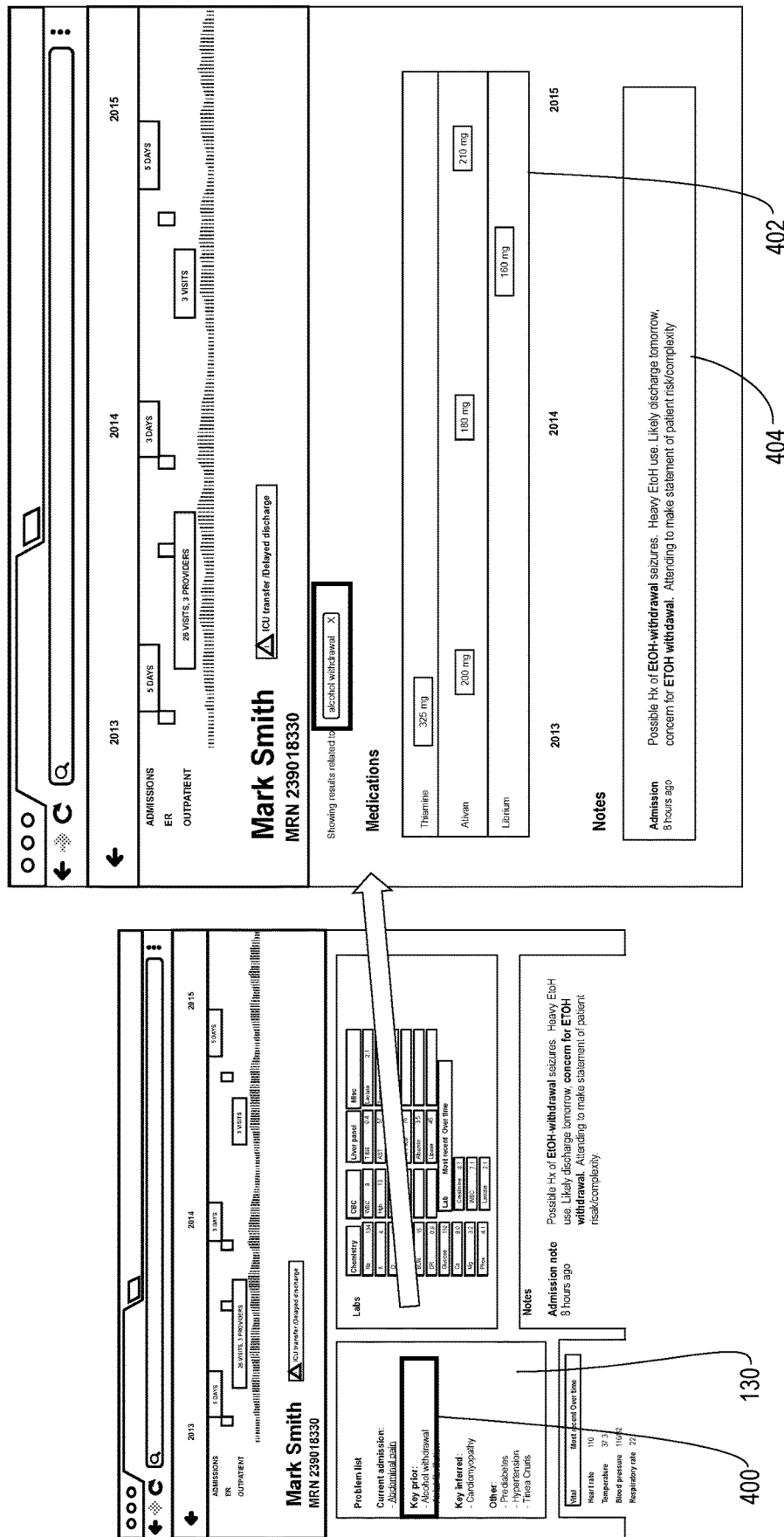
FIG. 18 shows the interface of FIG. 8B showing the ability of the interface to summarize each medical problem that is listed. In this instance, the provided clicked on the "alcohol withdrawal" key problem in the display of FIG. 8B and the display shows medications, notes and a timeline of events related to the key problem.

FIG. 18 shows the interface of FIG. 8B showing the ability of the interface to summarize each medical problem that is listed. In this instance, the provider clicked on the "alcohol withdrawal" key problem 400 in the display area 130 of FIG. 8B and the display shows medications in field 402, notes or excerpts thereof in field 404, and a timeline of events in field 406 related to the key problem of alcohol withdrawal.

Figure 19:
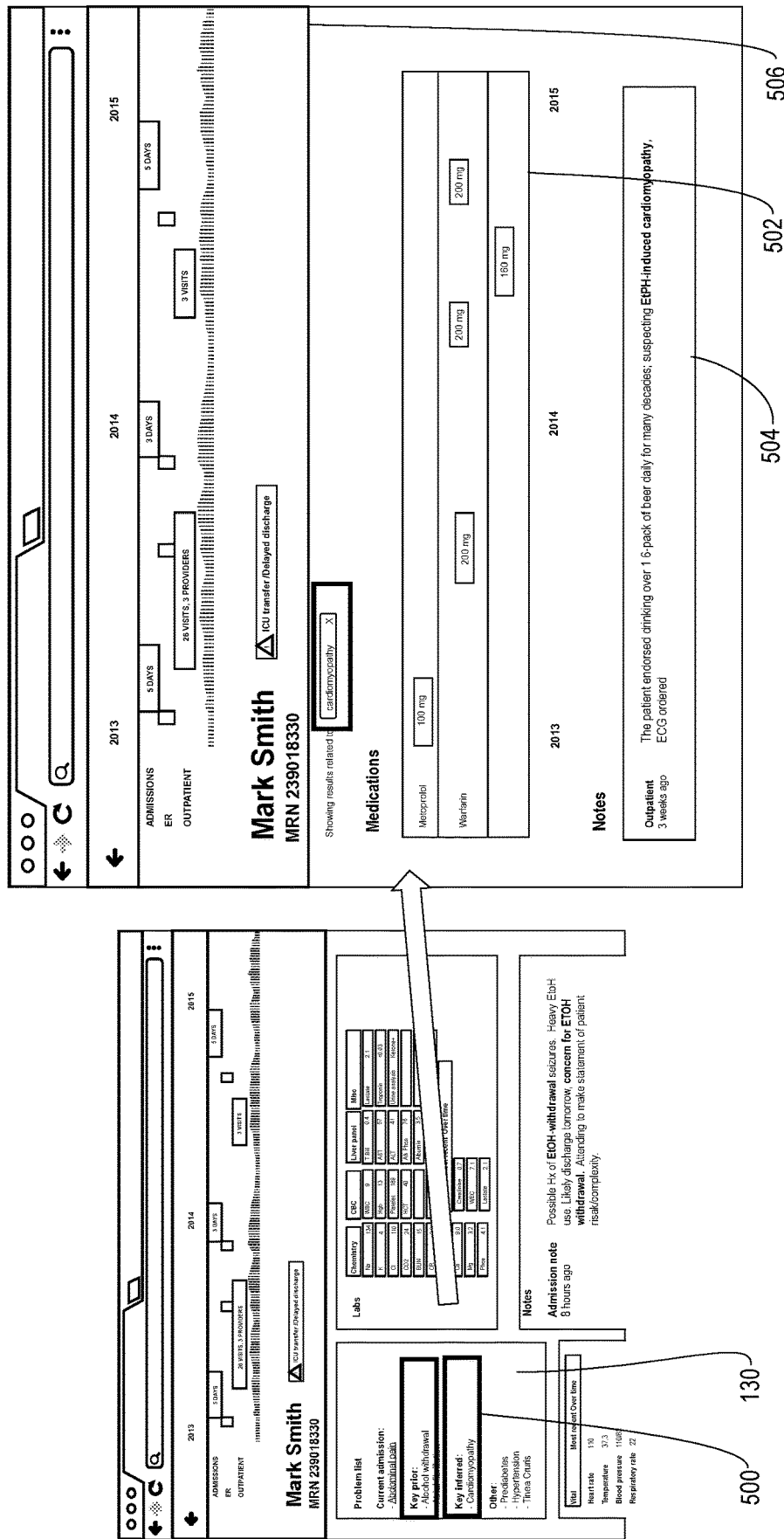
FIG. 19 shows the summary of the key problem "cardiomyopathy", in the form of a time line, medications and associated notes.

FIG. 19 shows what happens when the user selects the "key inferred" problem of cardiomyopathy, and the display shows a summary of the key problem "cardiomyopathy", in the form of a time line 506, medications 502 and associated notes or excerpts thereof in field 504. The notes or excerpts in the field 504 and 404 again use highlighting (bold, font size etc.) to indicate the results of the attention mechanism in the model to again show the physician the elements of the EHR that were most significant in generating the prediction.

Returning again to the description of the treatment of patient Mark Smith using the features of this disclosure, whereas in Example 1 Dr. Kingsley got the sepsis page at 1 am, with the features of this disclosure, Dr. Kingsley orders desired interventions early. She goes to see the patient immediately after the Alert is presented, and orders a CIWA protocol for alcohol withdrawal given the very high risk. She sees the outpatient suspicion of cardiomyopathy, and decides not to give 2L IV in case the patient actually has heart-failure. Given the diagnostic uncertainty, she decides to also order an ECG given the history of atrial fibrillation and examines the patient.

In summary, the system of this disclosure avoided the need to transfer the patient to the ICU and also be readmitted to the hospital later. In this Example, the physician is given timely alerts of predicted clinical events, presented with key medical events to the prediction, enabling the physician to improve their care for the patient, avoid the ICU transfer, avoid the unplanned readmission to the hospital and avoid the complications from administration of the antibiotics.

Example 3—Outpatient Alerts of Risk of ER or Hospitalization

This example will explain the use of the system of FIG. 1 in an outpatient setting.

Jennifer Choi is an 83 year-old woman with a history of heart failure (EF 30%), atrial fibrillation on warfarin, hypertension and prediabetes, presenting as a new patient at Dr. Keyes' outpatient cardiology clinic. Dr. Keyes was asked to manage her heart-failure. Ms. Choi wants to make sure Dr. Keyes understands her other conditions to make sure none of the treatments interfere with one-another.

Earlier, Ms. Choi had her labs prior to a primary care physician (PCP) visit where she was noted to have mild acute-kidney injury. Her PCP felt her volume status was stable, so he decreased the dose of diuretics and recommended repeat labs in a week.

On the way out the door from the appointment with Dr. Keyes, Ms. Choi's daughter privately expressed concern that her mother was increasingly confused and was worried she may not be taking her medications correctly. Dr. Keyes, already 30 minutes behind her schedule, said that she'd look into that further in an appointment in 3 weeks time, and put a reminder in her note to address confusion at the next visit: "Daughter is concerned patient is increasingly confused. Plan for MOCA and evaluation for cognitive impairment at next visit"

Both the PCP and Dr. Keyes participate in the system of FIG. 1 and forward the EHR of Ms. Choi to the computer 26 of FIG. 1 for application of the predictive models. Both the PCP and Dr. Keys have electronic devices (workstations) that include the interface of FIG. 9 which is used for outpatients.

The models predict that Ms. Choi is at risk for ED visit/hospitalization in the next 14 days. The alert is presented on the display of FIG. 9. That team has expertise to manage these high-risk situations. The display would show a timeline (including recent hospitalizations), such as shown in FIG. 18, field 406, it would show inferred problems: CHF, AKI, AFib, prediabetes, hypertension in the field 130 of FIG. 8B, and would include in the field 150 (FIG. 8B) excerpts of notes:

Note 1 (pcp): "Daughter is concerned patient is increasingly confused. Plan for MOCA and evaluation for cognitive impairment at next visit [. . . ] Patient has worsening renal function, likely from over-diuresis. WII decrease dose of lasix and repeat labs in 1 week. Told daughter to monitor weight and breathing".

Note 2 (nurse): "Patient is confused about lasix dose"

Note 3 (nurse): "I don't know what dose my mom should be taking"

As a result of the use of attention models, key portions of these notes are rendered in bold font-"concerned" "confused", "MOCA", "worsening renal function" "decrease dose of lasix" "confused about lasix dose", etc.

Example 4—A Busy Emergency Department

This example will illustrate the use of the features of this disclosure with the hypothetical patient "Mark Smith" in Example 1 and 2.

Mark Smith walks into the Emergency Room, clutching his stomach, complaining of pain. His heart-rate is 110, he is shaky, sweating and diuphretic. The nurse pulls in Dr. Peters, the ED resident, to help figure out what is going on.

Dr. Peters has numerous questions. Has he ever been in before? What diseases does he have? How severe are they? How have they been treated? The ED pulls up Mr. Smith's EHR and the predictive models of FIG. 1 are applied to his EHR. The interface of the terminal or other electronic device presenting the interface pulls up and displays information that is pertinent to these questions and his current chief complaint, and includes predicted diagnosis and key underlying medical events as shown in FIG. 8B. As current vital signs are obtained they are added to the display of pertinent chart information.

Further Considerations

The precise physical location and implementation of the predictive models and related computer or computer system 26 may vary. In some instances it may be physically located at a medical system or hospital serving affiliated facilities, primary care physician offices, and related clinics etc. In other situations it may be centrally located and receive EHRs and transmit predicted future clinical events and related prior medical events over wide area computer networks and service a multitude of unrelated healthcare institutions in a fee for service, subscription, standalone product, or other business model. In all situations appropriate data security and HIPAA compliance procedures are in place.

We claim:

1. A system, comprising in combination:
   a) computer memory storing aggregated electronic health records from a multitude of patients of diverse age, health conditions, and demographics including as elements thereof at least medications, laboratory values, diagnoses, vital signs, and free text medical notes, and obtained in different formats, wherein the aggregated electronic health records are converted into a single standardized data structure format and ordered per patient into an ordered arrangement; and
   b) a computer executing one or more deep learning models trained on the aggregated health records converted into the single standardized data structure format and in the ordered arrangement to predict one or more future clinical events based on an input electronic health record of a patient, and wherein a particular one of the one or more deep learning models includes an attention mechanism indicating how much attention the particular model gave to elements in the input electronic health record to predict the one or more future clinical events, wherein the particular model generates an output comprising both the predicted one or more future clinical events and the result of the attention mechanism, and wherein the computer executing the particular model of the one or more deep learning models comprises (1) generating, for a plurality of the elements of the input electronic health record, a respective data embedding vector and a respective time embedding vector, wherein generating the time embedding vector for a particular element of the input electronic health record comprises determining, based on a timing of the particular element, a plurality of single-valued functions of the timing of the particular element, (2) concatenating the data embedding vectors in an order to generate a data embedding matrix and concatenating the time embedding vectors in the same order to generate a time embedding matrix, (3) combining the time embedding matrix with a product of a projection matrix and the data embedding matrix to generate an attention vector as the result of the attention mechanism, and (4) predicting the one or more future clinical events based on the data embedding matrix and the attention vector.

2. The system of claim 1, wherein the aggregated health records comprise health records arranged in different data formats.

3. The system of claim 1, wherein the standardized data structure format comprises Fast Health Interoperability Resources (FHIR).

4. The system of claim 1, wherein the aggregated health records contain hospitalization diagnoses, and wherein the diagnoses are mapped to single-level Clinical Classification Software (CCS) codes.

5. The system of claim 1, wherein combining the time embedding matrix with the product of the projection matrix and the data embedding matrix to generate the attention vector comprises using a column dot product operator to multiply the product of the projection matrix and the data embedding matrix with the time embedding matrix.

6. A method of generating training data for machine learning from a set of raw electronic health records of a multitude of patients from diverse sources in diverse data formats, comprising the steps of:
   a) obtaining the set of raw electronic health records;
   b) converting the set of raw electronic health records into a single standardized data structure format;
   c) ordering the electronic health records converted into the single standardized data structure format into a time-sequenced order per patient; and
   d) storing the time-sequenced ordered electronic health records in the standardized data structure format in a data storage device; and
   using the time-sequenced ordered electronic health records in the standardized data structure format to train one or more deep learning models to predict one or more future clinical events based on an input electronic health record of a patient, wherein a particular one of the one or more deep learning models includes an attention mechanism indicating how much attention the particular model gave to elements in the input electronic health record to predict the one or more future clinical events, wherein the particular model generates an output comprising both the predicted one or more future clinical events and the result of the attention mechanism, and wherein executing the particular model of the one or more deep learning models comprises (1) generating for a plurality of the elements of the input electronic health record, a respective data embedding vector and a respective time embedding vector, wherein generating the time embedding vector for a particular element of the input electronic health record comprises determining, based on a timing of the particular element, a plurality of single-valued functions of the timing of the particular element, (2) concatenating the data embedding vectors in an order to generate a data embedding matrix and concatenating the time embedding vectors in the same order to generate a time embedding matrix, (3) combining the time embedding matrix with a product of a projection matrix and the data embedding matrix to generate an attention vector as the result of the attention mechanism, and (4) predicting the one or more future clinical events based on the data embedding matrix and the attention vector.

7. The method of claim 6, wherein the standardized data structure format comprises Fast Health Interoperability Resources (FHIR).

8. The method of claim 7, wherein the set of electronic health records includes both structured data and unstructured data including free text notes.

* * * * *